United States Patent
Sato et al.

(10) Patent No.: US 6,426,369 B1
(45) Date of Patent: Jul. 30, 2002

(54) OXETHAZAINE AS ANTIMICROBIAL AGENT

(75) Inventors: Masaru Sato, Saitama; Makoto Hadano, Tokyo, both of (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/486,607
(22) PCT Filed: Sep. 3, 1998
(86) PCT No.: PCT/JP98/03940
  § 371 (c)(1),
  (2), (4) Date: Mar. 1, 2000
(87) PCT Pub. No.: WO99/13872
  PCT Pub. Date: Mar. 25, 1999

(30) Foreign Application Priority Data

Sep. 17, 1997 (JP) .............................. 9-252552

(51) Int. Cl.$^7$ .............................. A31K 31/16
(52) U.S. Cl. ........................ 514/616; 514/339
(58) Field of Search ................... 514/616, 339

(56) References Cited

U.S. PATENT DOCUMENTS

| | | | |
|---|---|---|---|
| 4,447,437 A | * 5/1984 | Ohnishi et al. | 424/263 |
| 5,795,909 A | * 8/1998 | Shashoua et al. | 514/449 |
| 5,811,547 A | * 9/1998 | Nakamichi et al. | 540/589 |

OTHER PUBLICATIONS

Masuda et al, Biochem. Pharm., vol. 53(2), pp 1179–1787, 1987.*
Merck Index, 11th Edition, p. 1097, 6888, 1989.*
Hirschl et al., 1986, p. 45–49, Z. Antimikrob. Antineoplast. Chemother., vol. 4, No. 2.
Marshall et al., 4/85, 436–439, Med. J. Aust. 142.
Morris et al., 1987, p. 192–199, The American Journal of Gastroenterology, vol. 82, No. 3.
Rauws et al., 1988, p. 33–40, Gastroenterology, vol. 94, No. 1.
Yoshikawa et al., 1996, p. 828–831, Pharmacia, vol. 32, No. 7.
Marshall et al., 12/88, p. 1437–1442, The Lancet 351.
Hirchl A. et al., "Die Empfindlichkeit von Campylobacter pyloridis gehenuber antimikrobiellen Chemotherapeutika and Ulcustherapeutika" Z. Animikrob. Antineoplast. Chemother., 1986, vol. 4, No. 2, pp. 45–49.
Axon Scand. J. Gastroenterol 1994; 29 Suppl 105:31–7 "The Role of Omeprazole and Antibiotic Combinations in the Eradication of *Helicobacter pylori*—An Update".
Hopkins Gastroenterlogy 1996; 110: 1244–1252 "Relationship Between *Helicobacter pylori* Eradication and Reduced Duodenal and Gastric Ulcer Recurrence: A Review".
Rune Scand J Gastroenterol 1994; 29 Suppl 204:45–7 Treatment Strategies for Symptom Resolution, Healing, and *Helicobacter pylori* Eradication in Duodenal Ulcer Patients.
Fukuda Scand J. Gastroenterol 1996; 31 Suppl 214:54–55 "Suppression of *Helicobacter pylori* Colonization Omeprazole".

* cited by examiner

Primary Examiner—Shailendra Kumar
(74) Attorney, Agent, or Firm—Nixon & Vanderhye P.C.

(57) ABSTRACT

The present invention relates to an antimicrobial agent for preventing, ameliorating and treating diseases attributable to *Helicobacter pylori*, for example peptic ulcer and gastritis, particularly recurring peptic ulcer and recurring gastritis, and provides (1) an antimicrobial agent comprising oxethazaine represented by the following formula as an active ingredient, (2) an antimicrobial agent comprising oxethazaine and a proton pump inhibitor as active ingredients, and (3) an antimicrobial agent comprising oxethazaine and an antibiotic as active ingredients.

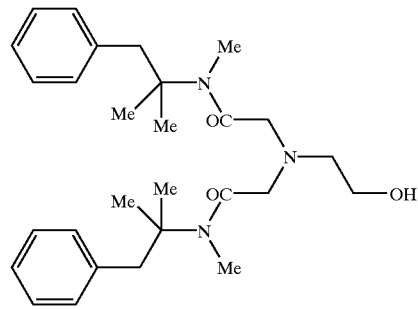

4 Claims, 4 Drawing Sheets

US 6,426,369 B1

OXETHAZAINE AS ANTIMICROBIAL AGENT

This application is a 371 of PCT/JP98/03940, filed Sep. 3, 1998.

1. Field of the Invention

The present invention relates to an antimicrobial agent for preventing, ameliorating and treating diseases caused by the microaerophilic Gram-negative spiral and short bacillus *Helicobacter pylori* (*H. pylori*), for example peptic ulcer and gastritis, particularly recurring peptic ulcer and gastritis.

2. Prior Art

Conventionally, a large number of medicines have been used as anti-ulcer agents for preventing, ameliorating and treating peptic ulcer such as gastric ulcer and duodenal ulcer, and recently, histamine $H_2$-receptor antagonists among these medicines are mainly used. By the advent of histamine $H_2$-receptor antagonists, it became possible to rapidly ameliorate and treat peptic ulcer and gastritis, particularly with respect to subjective symptoms. However, in the treatment of peptic ulcer or gastritis by the conventional anti-ulcer agents containing histamine $H_2$-receptor antagonists, there is the problem that ulcer recurs highly frequently when chemotherapy is suspended after the recovery. Because the reason for this recurrence has not been revealed for a long time, none of effective prophylactic and therapeutic methods have been established.

Meanwhile, it was shown from 1979 onward that the microaerophilic Gram-negative spiral and short bacillus *H. pylori* is present in gastric mucosa of patients suffering from peptic ulcer and bacterium has a close relationship with gastritis and gastric ulcer. It, formerly classified as *Campylobacter pylori* (*C. pylori*), was newly designated *H. pylori* in re-consideration in microbial taxonomy in 1989, and thus *C. pylori* and *H. pylori* are the same bacterium although it may be referred to as *C. pylori* in some literatures.

As literatures showing the relationship between *H. pylori* and gastric ulcer or gastritis, e.g. Med. J. Aust., 142, 436–439, 1985 and Am. J. Gastroentel., 82, 192–199, 1987 reported that acute gastritis occurred upon oral administration of *H. pylori* to healthy volunteers.

Further, the attention has been directed to the relationship between *H. pylori* and gastritis or peptic ulcer, since it was also reported in Gastroentel., 94, 33–40, 1988 that when an antibiotic is administered to patients suffering from peptic ulcer to eradicate *H. pylori*, the improvement of an image of gastric tissues is recognized.

In addition, Lancet, 1437–1442, 1988 reported that the frequency of recurrence of peptic ulcer is high in *H. pylori*-positive patients suffering from peptic ulcer as compared with *H. pylori*-negative patients, and it was thus revealed that the eradication of *H. pylori* is essential for prevention and treatment of recurring peptic ulcer.

Further, recently, the relationship between *H. pylori* and the generation of gastric cancer has been discussed enthusiastically, and the importance of eradication of *H. pylori* came to be recognized more strongly.

As medicines capable of eradicating *H. pylori*, antibiotics such as penicillin, cephalosporin, tetracycline, neuquinolone, and macrolide antibiotics, and some anti-ulcer agents such as praunotol, sofalcone, benexate hydrochloride (betadex), bismuth preparations, and a proton pump inhibitor (referred to hereinafter as PPI) may be proposed.

Among the above-mentioned known medicines capable of eradicating *H. pylori*, anti-ulcer agents other than PPI have a very weak action for eradication of *H. pylori*, and thus the effect of these anti-ulcer agents in eradication could not be expected in clinically ordinary doses.

On the other hand, PPI is recognized to have stronger efficacy, but the eradication of *H. pylori* by PPI alone is difficult.

Further, the in vitro action of the antibiotics in eradication is very strong, but they are rapidly degraded in gastric acid because of very weak physical properties against acid, so there is the problem that their in vivo or clinical effect could not be recognized to be so significant as expected. Further, the antibiotics are administered for eradicating *H. pylori* in larger doses than clinically ordinary doses, thus causing frequently occurring side effects such as anaphylaxis and diarrhea, and when used for a long period of time, the antibiotics bring about many problems such as occurrence of non-recovering severe side effects such as impediments of organs and blood, and generation of resistant bacteria.

As described above, medicines by which recurring peptic ulcer and gastritis attributable to *H. pylori* can be clinically prevented and treated reliably and safely for a prolonged period of time, have never been found yet and there has been demand for a new medicine.

The study during this period is described in e.g. Pharmacia, 32 (7), 828–831, 1996, that is:

(1) The $H_2$-receptor antagonist did not have an antimicrobial action on *H. pylori*.

(2) The degree of efficacy for *H. pylori* therapy by PPI alone (lansoprazole, 30 mg/day, 8 weeks) was as very low as 5%.

(3) The effect of a single antibiotic in eradication was also very low.

(4) Accordingly, combined therapy by multiple drugs and combined therapy by PPI are considered to be effective, and particular attention is paid to combined therapy by PPI and an antibiotic; however, even combined therapy using 2 drugs, that is, lansoprazole+clarithromycin or omeprazole+amoxicillin, did not achieve any satisfactory effect for eradication of the microorganism.

(5) Accordingly, combined therapy simultaneously using 3 medicines, that is, PPI plus 2 antibiotics, has also been attempted recently.

Such extreme combined therapy by multiple drugs has many disadvantages that administration for a long time is cumbersome and difficult and occurrence of side effects is increased significantly, and thus it cannot be said that such therapy is preferable for the patient.

Under these circumstances, the development of a medicine which in an ordinary dose, exhibits a satisfactory action on eradication of *H. pylori* and is highly safe even when used for a long time has been continued.

DISCLOSURE OF THE INVENTION

Accordingly, the present inventors have conducted extensive studies for a medicine which satisfies such requirements i.e. a clinically more potent action on eradication of *H. pylori* and high safety even when administered for a prolonged period of time. As a result, they unexpectedly found that oxethazaine, which is used clinically widely as a local anesthetic for digestive-tract mucosa, achieved the desired object as an antimicrobial agent. Further, they found that a combination of oxethazaine and PPI brings about synergism or additive effect on eradication of *H. pylori*, thus achieving further preferable therapeutic effects, while a combination of oxethazaine and an antibiotic or a $H_2$-receptor antagonist can lead to a reduction of the dose of the antibiotic or $H_2$-receptor antagonist administered, and thus completed the present invention.

Accordingly, the object of the present invention is to provide an antimicrobial agent which is clinically highly effective against *H. pylori*, specifically a prophylactic, therapeutic and ameliorating agent for peptic ulcer and gastritis, particularly a prophylactic, therapeutic and ameliorating agent for recurring ulcer and recurring gastritis, consequently enabling prevention of gastric cancer.

Oxethazaine according to the present invention has the chemical name 2,2'-[(2-hydroxyethyl)amino]bis[N-(1,1-dimethyl-2-phenylethyl)-N-methylacetamide], which is represented by the following formula:

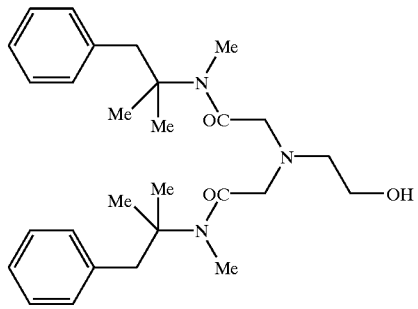

Oxethazaine is used pharmacologically as a local anesthetic for digestive-tract mucosa to treat pains, acid symptoms, nausea, emesis, stomach discomfort, an impending need to defecate etc., which are accompanied by esophagitis, gastritis, gastric and duodenal ulcer, and colon hypersensitivity.

Further, oxethazaine unlike antibiotics does not permit appearance of resistant bacteria, and thus it can be expected that its therapeutic effect is stable for a prolonged period of time.

Oxethazaine can be produced by a method described in U.S. Pat. No. 2,780,646.

The present invention provides an antimicrobial agent comprising oxethazaine as an active ingredient; an antimicrobial composition comprising oxethazaine and a proton pump inhibitor as active ingredients; an antimicrobial composition comprising oxethazaine and an antibiotic as active ingredients; and an antimicrobial composition comprising oxethazaine and a $H_2$-receptor antagonist or its pharmacologically acceptable salt as active ingredients.

The present invention provides a method of treating a disease attributable to *Helicobacter pylori*, which comprises the step of administering an effective amount of oxethazaine to a patient suffering from the disease. In the present invention, oxethazaine is used for production of an antimicrobial agent.

In the present invention, the action of eradicating *H. pylori* can be expected by use of oxethazaine alone, but when it is combined with PPI, the synergism, or additive effect of both the compounds can be expected. Here, PPI is not particularly limited insofar as it is a medicine having a proton pump inhibitory effect. Usually, it is a compound having a benzimidazole skeleton, and specific examples include rabeprazole (I), 2-[4-(3-methoxypropoxy)-3-methylpyridine-2-yl]methylthio-1H-benzimidazole (II), omeprazole (III), lansoprazole (IV) and pantoprazole (V), or pharmacologically acceptable salts thereof.

The chemical formulae of these specific examples are shown below.

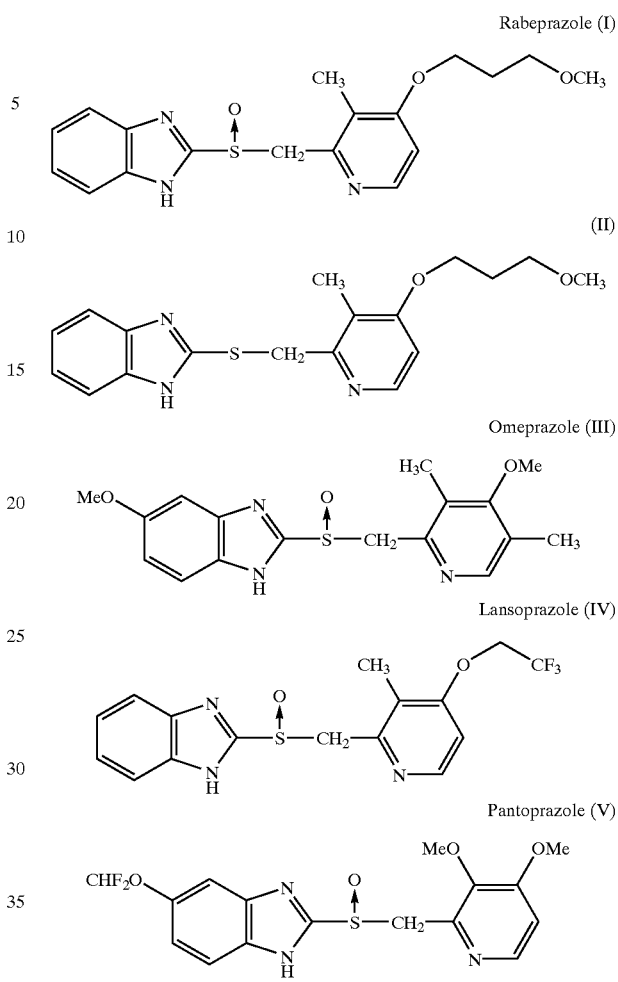

It is possible to produce rabeprazole (I) and 2-[4-(3-methoxypropoxy)-3-methylpyridine-2-yl]methylthio-1H-benzimidazole (II) according to the method described in JP-A 64-6270, omeprazole (III) according to the method in JP-A 54-141783, lansoprazole (IV) according to the method in JP-A 61-50978 and pantoprazole (V) according to the method in JP-A 61-22079.

Additionally, in the present invention, the dose of an antibiotic can also be reduced by combined use of oxethazaine and the antibiotic.

The antibiotics in the present invention are not limited insofar as they are medicines having an antimicrobial effect, and specific examples include e.g. penicillin antibiotics such as ampicillin (ABPC) and amoxicillin (AMPC), neuquinolone antibiotics such as ofloxacin (OFLX), macrolide antibiotics such as erythromycin (EM), roxithromycin (RXM) and clarithromycin (CAM), tetracycline antibiotics such as minocycline(MINO), antitrichomonas such as metronidazole. These may be used singly or in combination thereof.

Further, in the present invention, oxethazaine is combined with a $H_2$-receptor antagonist or its pharmacologically acceptable salt, whereby the synergism, or additive effect of both the compounds can be expected. Here, the $H_2$-receptor antagonist means histamine $H_2$-receptor antagonist, and specific examples include cimetidine, ranitidine hydrochloride, famotidine etc.

In the present invention, the pharmacologically acceptable salt includes e.g. addition salts of inorganic acids, such as hydrochloride, sulfate, nitrate, phosphate, hydrobromate, hydriodate and perchlorate, addition salts of organic acids, such as oxalate, maleate, fumarate, succinate, methane sulfonate, benzene sulfonate, p-toluene sulfonate and camphor sulfonate, and addition salts of metals, such as sodium salt, potassium salt, calcium salt and magnesium salt. Among these, more preferable salts include sodium salt as the proton pump inhibitor, and hydrochloride as the $H_2$-receptor antagonist.

Accordingly, an object of the present invention is to provide an antimicrobial agent having *H. pylori*-eradicating action equal to or higher than that of antibiotics, being highly safe even when administered for a long time, and having clinically excellent usefulness for peptic ulcer and gastritis, particularly for recurring ulcer or recurring gastritis, consequently enabling prevention of gastric cancer.

Further, it is also an object of the present invention to reduce the dose of PPI, an antibiotic or a $H_2$-receptor antagonist by combining oxethazaine with PPI, the antibiotic or the $H_2$-receptor antagonist, thus preventing and/or reducing side effects or improving compliance.

Figure 1:
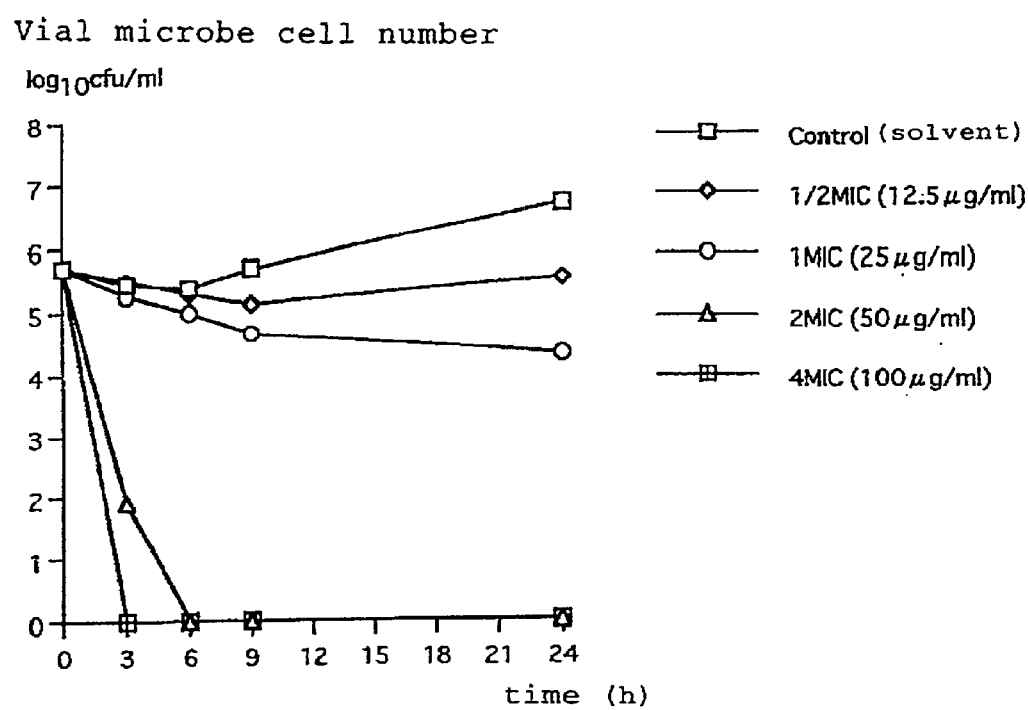
FIG. 1 is a graph showing the sterilizing effect (change with time) of oxethazaine on *H. pylori* NCTC 11637 (standard strain)

Hereinafter, examples of antimicrobial activity tests are given to demonstrate the effect of the present invention.

Antimicrobial Activity Test 1

Anti-*H. pylori* Activity of a Single Compound

1. Method

The in vitro antimicrobial activity of each of the following test compounds on 25 kinds of *H. pylori* strains i.e. standard strains and clinically separated strains (derived from gastric mucosa) was evaluated by the standard method (agar plate method) according to the Chemotherapy Society of Japan.

That is, the test plate agar medium used was Brucella agar (BBL microbiology Systems™ manufactured by Vector Dickinson & Co.) to which horse fiber-free blood had been added at a concentration of 7%, and cultured at 37° C., pH 7.0 for 3 days under slightly aerobic conditions (Canpipack™ manufactured by Vector Dickinson & Co.) to judge whether the growth was inhibited or not at each concentration (μg/ml) of the test compound.

2. Test Compounds
(1) Oxethazaine
(2) 2-[4-(3-Methoxypropoxy)-3-methylpyridine-2-yl] methylthio-1H-benzimidazole (II)
(3) Omeprazole (III)
(4) Lansoprazole (IV)

For use, each of the above-mentioned test compounds was dissolved in a 1% aqueous solution of N,N-dimethyl sulfoxide (DMSO).

3. Results

The results are shown below. Among the test strains in the table, NCTC 11637, NCTC 11639 and NCTC 11916 are standard strains, and the others are clinically separated strains.

| Strain No. | Compound | | | |
| --- | --- | --- | --- | --- |
| | Oxethazaine | (II) | (III) | (IV) |
| NCTC11637 | 25 | 1.56 | 50 | 12.5 |
| NCTC11639 | 50 | 0.8 | 25 | 3.13 |
| NCTC11916 | 25 | 1.56 | 50 | 6.25 |
| EH12 | 25 | 0.8 | 25 | 3.13 |
| EH13 | 25 | 0.8 | 25 | 3.13 |
| EH16 | 25 | 0.8 | 25 | 3.13 |
| EH26 | 25 | 1.56 | 25 | 6.25 |
| 90-384 | 25 | 1.56 | 50 | 3.13 |
| 90-390 | 25 | 0.8 | 50 | 3.13 |
| 89-357 | 25 | 0.8 | 50 | 6.25 |
| 90-428 | 25 | 1.56 | 50 | 6.25 |
| 89-360 | 25 | 1.56 | 50 | 6.25 |
| 89-360 (1) | 25 | 1.56 | — | 6.25 |
| 90-407 | 25 | 1.56 | 25 | 3.13 |
| 90-411 | 25 | 0.8 | 25 | 3.13 |
| 89-355 | 12.5 | 1.56 | 25 | 3.13 |
| 90-397 | 25 | 1.56 | 25 | 3.13 |
| 90-388 | 25 | 1.56 | 50 | 3.13 |
| 90-407 (1) | 25 | 0.8 | — | 6.25 |
| 90-388 (1) | 25 | 0.8 | 25 | 6.25 |
| 90-390 (1) | 25 | 0.8 | 25 | 6.25 |
| 90-414 | 25 | 0.8 | 50 | 6.25 |
| 90-397 | 25 | 0.8 | 25 | 6.25 |
| 90-414 (1) | 25 | 0.8 | 25 | 6.25 |
| 90-392 | 25 | 0.8 | 25 | 6.25 |

From the results of the antimicrobial activity test 1 described above, it is evident that the oxethazaine according to the present invention has excellent anti-*H. pylori* activity.

The clinical dose of oxethazaine administered as a local anesthetic for digestive-tractmucosa is comparatively high (15 to 40 mg/day), and thus the concentration of oxethazaine in gastric juice (which is secreted in an amount of about 500 ml/day) is 30 to 80 μg/ml, which exceeds MIC (about 25 μg/ml) for each strain confirmed in Table 1. Accordingly, satisfactory pharmacological effect can be expected even by use of oxethazaine alone.

Antimicrobial Activity Test 2

Comparison of Oxethazaine and an Antibiotic in Time for Sterilizing *H. pylori*

1. Method

NCTC 11637 and NCTC 11916 (standard strains) and EH 12 (clinically separated strain) were used as test strains.

A solution of the test compound was added to Brucella broth containing 5% fetal bovine serum, cultured under slightly aerobic conditions at 37° C., and the vial microbe cell number in Brucella agar containing 7% horse blood was counted at predetermined intervals.

2. Test Compounds
(1) Oxethazaine
(2) Ampicillin (ABPC)

The above compound (1) was dissolved in a 1% aqueous solution of N,N-dimethyl sulfoxide (DMSO), and the above compound (2) was dissolved in water to prepare a solution of each test compound.

3. Results

The results are shown below (see FIGS. 1 to 4).

"cfu" in Tables and Figures means "colony forming unit".

(1) The sterilizing effect of oxethazaine on NCTC 11637 (see FIG. 1)

| Concentration | Viable microbe cell number ($\log_{10}$cfu/ml) | | | | |
|---|---|---|---|---|---|
| | 0 h | 3 h | 6 h | 9 h | 24 h |
| Control | 5.70 | 5.43 | 5.36 | 5.68 | 6.68 |
| ½ MIC | 5.70 | 5.48 | 5.27 | 5.11 | 5.51 |
| 1 MIC | 5.70 | 5.24 | 4.98 | 4.64 | 4.30 |
| 2 MIC | 5.70 | 1.90 | 0 | 0 | 0 |
| 4 MIC | 5.70 | 0 | 0 | 0 | 0 |

Figure 2:
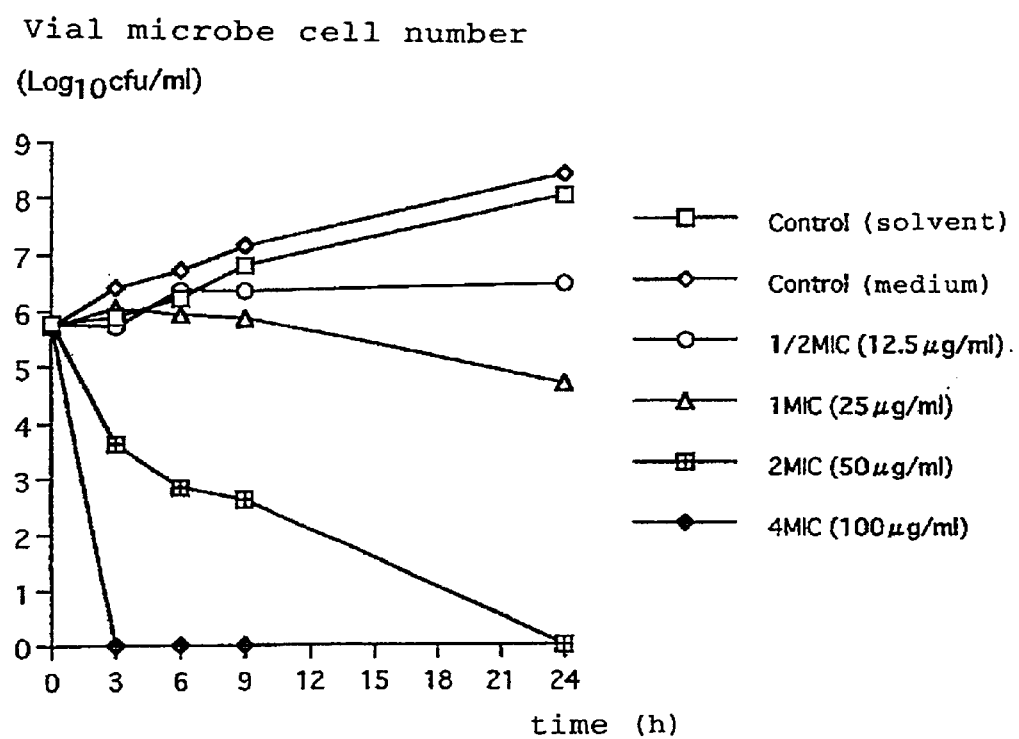
FIG. 2 is a graph showing the sterilizing effect (change with time) of oxethazaine on *H. pylori* NCTC 11916 (standard strain)

(2) The sterilizing effect of oxethazaine on NCTC 11916 (see FIG. 2)

| Concentration | Viable microbe cell number ($\log_{10}$cfu/ml) | | | | |
|---|---|---|---|---|---|
| | 0 h | 3 h | 6 h | 9 h | 24 h |
| Control (solvent) | 5.77 | 5.88 | 6.21 | 6.78 | 8.00 |
| Control (medium) | 5.72 | 6.40 | 6.70 | 7.12 | 8.38 |
| ½ MIC | 5.77 | 5.70 | 6.35 | 6.32 | 6.44 |
| 1 MIC | 5.72 | 6.04 | 5.92 | 5.84 | 4.67 |
| 2 MIC | 5.77 | 3.63 | 2.83 | 2.61 | 0 |
| 4 MIC | 5.77 | 0 | 0 | 0 | 0 |

Figure 3:
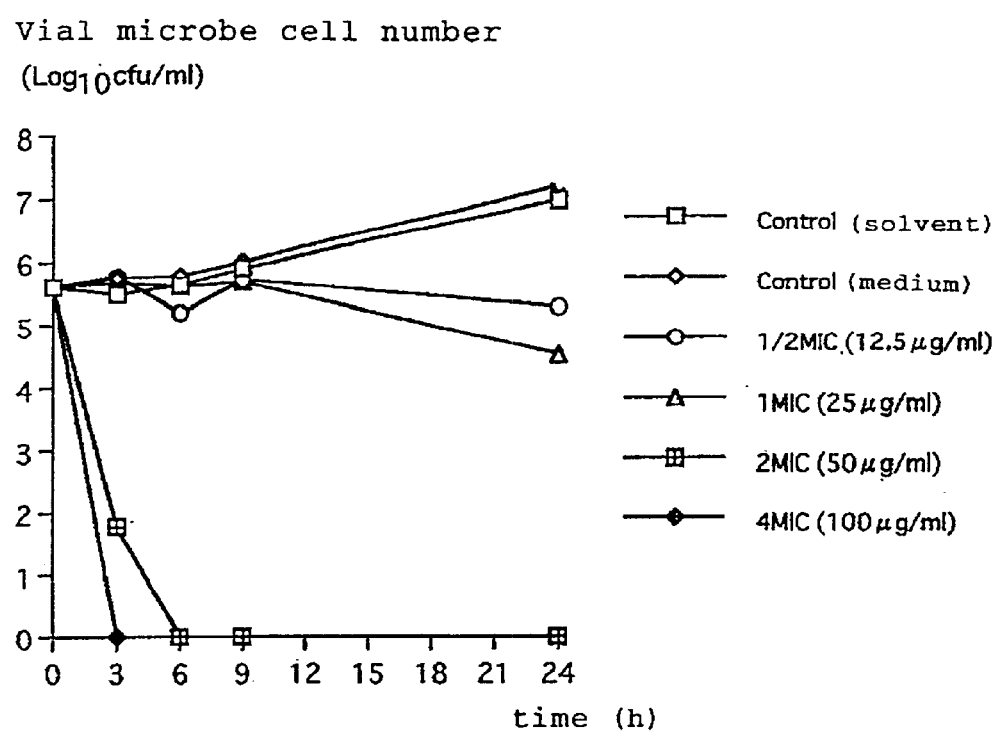
FIG. 3 is a graph showing the sterilizing effect (change with time) of oxethazaine on *H. pylori* EH 12 (clinically separated strain)

(3) The sterilizing effect of oxethazaine on EH12 (see FIG. 3)

| Concentration | Viable microbe cell number ($\log_{10}$cfu/ml) | | | | |
|---|---|---|---|---|---|
| | 0 h | 3 h | 6 h | 9 h | 24 h |
| Control (solvent) | 5.60 | 5.48 | 5.63 | 5.90 | 6.97 |
| Control (medium) | 5.60 | 5.74 | 5.78 | 6.00 | 7.18 |
| ½ MIC | 5.60 | 5.77 | 5.19 | 5.71 | 5.27 |
| 1 MIC | 5.60 | 5.67 | 5.61 | 5.68 | 4.51 |
| 2 MIC | 5.60 | 1.78 | 0 | 0 | 0 |
| 4 MIC | 5.60 | 0 | 0 | 0 | 0 |

Figure 4:
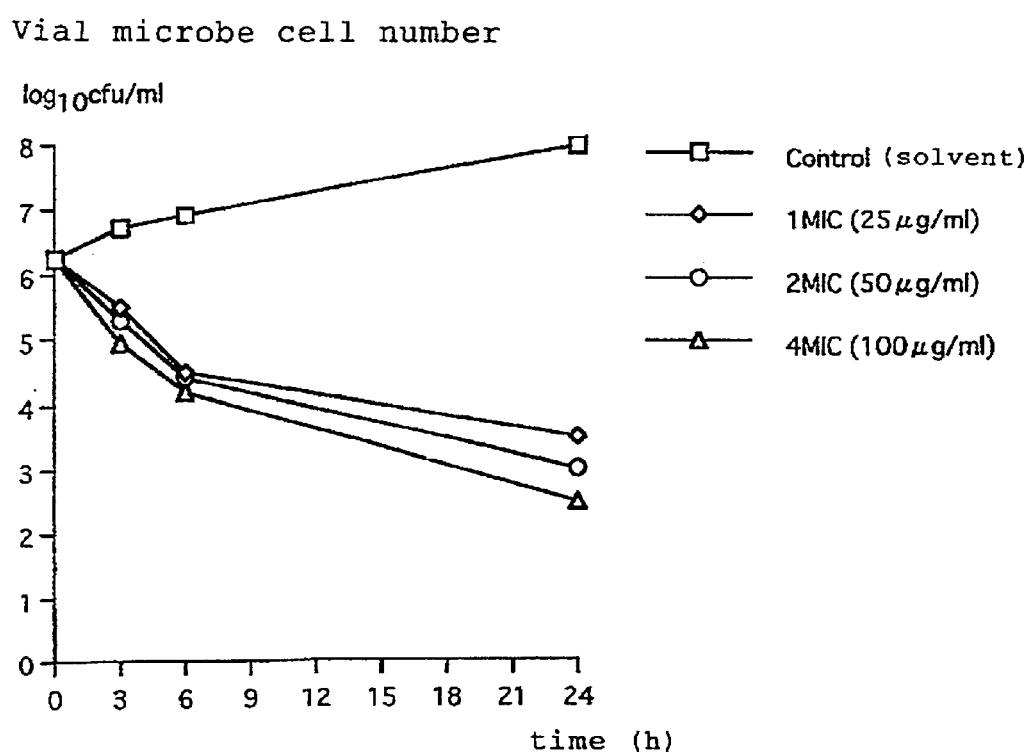
FIG. 4 is a graph showing the sterilizing effect (change with time) of an antibiotic (ampicillin) on *H. pylori* NCTC 11637 (standard strain).

(4) The sterilizing effect of ampicillin on NCTC 11637 (see FIG. 4)

| Concentration | Viable microbe cell number ($\log_{10}$cfu/ml) | | | |
|---|---|---|---|---|
| | 0 h | 3 h | 6 h | 24 h |
| Control | 6.25 | 6.71 | 6.90 | 7.94 |
| 1 MIC | 6.25 | 5.51 | 4.49 | 3.48 |
| 2 MIC | 6.25 | 5.30 | 4.41 | 3.00 |
| 4 MIC | 6.25 | 4.95 | 4.20 | 2.48 |

As is evident from the above results and FIGS. 1 to 4, the antibiotic shows a gentle sterilization curve, whereas oxethazaine according to the present invention shows a rapidly dropping sterilization curve.

This suggests that oxethazaine is more immediate-acting in exhibiting clinical sterilizing effect than the antibiotic, and as compared with the antibiotic, the excellent effect of the present invention is evident.

Antimicrobial Activity Test 3

Anti-*H. pylori* Activity of Oxethazaine used in Combination with Compound (II)

1. Method

The effect of oxethazaine used in combination with compound (II) (2-[4-(3-methoxypropoxy)-3-methylpyridine-2-yl]methylthio-1H-benzimidazole) was examined in the same manner as in antimicrobial activity test 1, using a checker board method.

2. Results

Hereinafter, the results are shown for each strain.

In each Table, the concentration of oxethazaine is shown vertically, and the concentration of compound (II) is shown horizontally.

In each Table, "−" indicates the inhibited growth of *H. pylori* (presence of antimicrobial activity), and "+" indicates the growth of *H. pylori* (absence of antimicrobial activity).

The synergism or additive effect in the present invention has the following meanings.

(1) Synergism

It is assumed to be present when the MICs of both oxethazaine and PPI are reduced by ¼ or more (when anti-*H. pylori* activity is recognized even when the concentrations of both oxethazaine and PPI are reduced to ¼.).

(2) Additive Effect

It is assumed to be present when the MIC of either oxethazaine or PPI is reduced by ½ (when anti-*H. pylori* activity is not recognized when the concentrations of both oxethazaine and PPI are reduced to ¼, but anti-*H. pylori* activity is recognized when the concentration of one compound is reduced to ¼ and simultaneously the concentration of the other compound is reduced to ½.).

TABLE 1

NCTC11637 (additive effect)

| Oxethazaine (μg/ml) | Compound (II) (μg/ml) | | | | | | | | | | | |
|---|---|---|---|---|---|---|---|---|---|---|---|---|
| | 100 | 50 | 25 | 12.5 | 6.25 | 3.13 | 1.56 | 0.8 | 0.4 | 0.2 | 0.1 | 0 |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | + | + | + |
| 6.25 | − | − | − | − | − | − | − | − | + | + | + | + |
| 3.13 | − | − | − | − | − | − | − | − | + | + | + | + |
| 0 | − | − | − | − | − | − | − | + | + | + | + | − |

In Table 1 above, a row of 25 (μg/ml) corresponds to the MIC of oxethazaine alone on NCTC 11637, and a row of 1.56 (μg/ml) corresponds to the MIC of compound (II) alone on the same strain.

At the concentration (6.25 μg/ml) of ¼ relative to the MIC of oxethazaine alone and at the concentration (0.4 μg/ml) of ¼ relative to the MIC of compound (II) alone, no anti-*H. pylori* activity was recognized.

However, when one of them was present at the concentration of ¼ and the other at the concentration of ½, anti-*H. pylori* activity was recognized.

Accordingly, when oxethazaine and compound (II) were used in combination, their additive effect on the above strain was recognized.

TABLE 2

NCTC11639 (synergism)

| Oxethazaine (μg/ml) | Compound (II) (μg/ml) | | | | | | | | | | | |
|---|---|---|---|---|---|---|---|---|---|---|---|---|
| | 100 | 50 | 25 | 12.5 | 6.25 | 3.13 | 1.56 | 0.8 | 0.4 | 0.2 | 0.1 | 0 |
| 100 | − | − | − | − | − | − | − | − | − | − | − | − |
| 50 | − | − | − | − | − | − | − | − | − | − | − | − |
| 25 | − | − | − | − | − | − | − | − | − | − | − | + |
| 12.5 | − | − | − | − | − | − | − | − | − | − | + | + |
| 6.25 | − | − | − | − | − | − | − | − | − | + | + | + |
| 3.13 | − | − | − | − | − | − | − | − | − | + | + | + |
| 0 | − | − | − | − | − | − | − | − | + | + | + | + |

Next, in Table 2 above, a row of 50 (μg/ml) corresponds to the MIC of oxethazaine alone on NCTC 11639, and a row of 0.8 (μg/ml) corresponds to the MIC of compound (II) alone on the same.

At the concentration (12.5 μg/ml) of ¼ relative to the MIC of oxethazaine alone and at the concentration (0.2 μg/ml) of ¼ relative to the MIC of compound (II) alone, anti-*H. pylori* activity was recognized.

Accordingly, when oxethazaine and compound (II) were used in combination, their synergism on the above strain was recognized.

Then, the effect of combined use was evaluated in the same manner.

TABLE 3

| Oxethazaine (μg/ml) | Compound (II) (μg/ml) | | | | | | | | | | | |
|---|---|---|---|---|---|---|---|---|---|---|---|---|
| | 100 | 50 | 25 | 12.5 | 6.25 | 3.13 | 1.56 | 0.8 | 0.4 | 0.2 | 0.1 | 0 |
| NCTC11916 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | + |
| 6.25 | − | − | − | − | − | − | − | − | + | + | + | + |

TABLE 3-continued

| Oxethazaine | Compound (II) (μg/ml) | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| 3.13 | − | − | − | − | − | − | − | − | + | + | + | + |
| 0 | − | − | − | − | − | − | − | + | + | + | + | |
| EH 12 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | + |
| 6.25 | − | − | − | − | − | − | − | − | − | + | + | + |
| 3.13 | − | − | − | − | − | − | − | − | + | + | + | + |
| 0 | − | − | − | − | − | − | − | − | + | + | + | |
| EH 13 (synergism) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | − | + |
| 6.25 | − | − | − | − | − | − | − | − | − | − | + | + |
| 3.13 | − | − | − | − | − | − | − | − | − | + | + | + |
| 0 | − | − | − | − | − | − | − | − | + | + | + | |

TABLE 4

| Oxethazaine | Compound (II) (μg/ml) | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| EH 16 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | + | + | + |
| 6.25 | − | − | − | − | − | − | − | − | − | + | + | + |
| 3.13 | − | − | − | − | − | − | − | − | + | + | + | + |
| 0 | − | − | − | − | − | − | − | − | + | + | + | |
| EH 26 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | + |
| 6.25 | − | − | − | − | − | − | − | − | + | + | + | + |
| 3.13 | − | − | − | − | − | − | − | − | + | + | + | + |
| 0 | − | − | − | − | − | − | − | + | + | + | + | |
| 90-384 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | + | + | + | + |
| 6.25 | − | − | − | − | − | − | − | − | + | + | + | + |
| 3.13 | − | − | − | − | − | − | − | − | + | + | + | + |
| 0 | − | − | − | − | − | − | − | + | + | + | + | |

TABLE 5

| Oxethazaine | Compound (II) (μg/ml) | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| 90-390 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | − | + |
| 6.25 | − | − | − | − | − | − | − | − | − | + | + | + |
| 3.13 | − | − | − | − | − | − | − | − | + | + | + | + |
| 0 | − | − | − | − | − | − | − | − | + | + | + | |

TABLE 5-continued

| Oxethazaine | Compound (II) (μg/ml) | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| | | | | 89-357 (additive effect) | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | + |
| 6.25 | − | − | − | − | − | − | − | − | + | + | + | + |
| 3.13 | − | − | − | − | − | − | − | − | + | + | + | + |
| 0 | − | − | − | − | − | − | − | − | + | + | + | |
| | | | | 90-428 (additive effect) | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | + |
| 6.25 | − | − | − | − | − | − | − | − | + | + | + | + |
| 3.13 | − | − | − | − | − | − | − | − | + | + | + | + |
| 0 | − | − | − | − | − | − | − | + | + | + | + | |

TABLE 6

| Oxethazaine | Compound (II) (μg/ml) | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| | | | | 89-360 (additive effect) | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | + |
| 6.25 | − | − | − | − | − | − | − | − | + | + | + | + |
| 3.13 | − | − | − | − | − | − | − | − | + | + | + | + |
| 0 | − | − | − | − | − | − | − | + | + | + | + | |
| | | | | 89-360(1) (additive effect) | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | + |
| 6.25 | − | − | − | − | − | − | − | − | + | + | + | + |
| 3.13 | − | − | − | − | − | − | − | − | + | + | + | + |
| 0 | − | − | − | − | − | − | − | + | + | + | + | |
| | | | | 90-407 (additive effect) | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | + |
| 6.25 | − | − | − | − | − | − | − | − | + | + | + | + |
| 3.13 | − | − | − | − | − | − | − | − | + | + | + | + |
| 0 | − | − | − | − | − | − | − | + | + | + | + | |

TABLE 7

| Oxethazaine | Compound (II) (μg/ml) | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| | | | | 90-411 (additive effect) | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | − |
| 6.25 | − | − | − | − | − | − | − | − | − | + | + | + |
| 3.13 | − | − | − | − | − | − | − | − | − | + | + | + |
| 0 | − | − | − | − | − | − | − | − | + | + | + | |

TABLE 7-continued

| Oxethazaine | Compound (II) (μg/ml) | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| 89-355 (synergism) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | − | − |
| 6.25 | − | − | − | − | − | − | − | − | − | − | + | + |
| 3.13 | − | − | − | − | − | − | − | − | − | + | + | + |
| 0 | − | − | − | − | − | − | − | + | + | + | + | |
| 90-397 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | + |
| 6.25 | − | − | − | − | − | − | − | − | + | + | + | + |
| 3.13 | − | − | − | − | − | − | − | − | + | + | + | + |
| 0 | − | − | − | − | − | − | − | + | + | + | + | |

TABLE 8

| Oxethazaine | Compound (II) (μg/ml) | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| 90-388 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | + |
| 6.25 | − | − | − | − | − | − | − | − | + | + | + | + |
| 3.13 | − | − | − | − | − | − | − | − | + | + | + | + |
| 0 | − | − | − | − | − | − | − | + | + | + | + | |
| 90-407(1) (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | + |
| 6.25 | − | − | − | − | − | − | − | − | + | + | + | + |
| 3.13 | − | − | − | − | − | − | − | − | + | + | + | + |
| 0 | − | − | − | − | − | − | − | + | + | + | + | |
| 90-388(1) (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | + |
| 6.25 | − | − | − | − | − | − | − | − | + | + | + | + |
| 3.13 | − | − | − | − | − | − | − | − | + | + | + | + |
| 0 | − | − | − | − | − | − | − | + | + | + | + | |

TABLE 9

| Oxethazaine | Compound (II) (μg/ml) | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| 90-390(1) (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | + |
| 6.25 | − | − | − | − | − | − | − | − | + | + | + | + |
| 3.13 | − | − | − | − | − | − | − | − | + | + | + | + |
| 0 | − | − | − | − | − | − | − | + | + | + | + | |

TABLE 9-continued

| Oxethazaine | Compound (II) (µg/ml) | | | | | | | | | | | |
|---|---|---|---|---|---|---|---|---|---|---|---|---|
| (µg/ml) | 100 | 50 | 25 | 12.5 | 6.25 | 3.13 | 1.56 | 0.8 | 0.4 | 0.2 | 0.1 | 0 |
| | | | | 90-414 (additive effect) | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | + |
| 6.25 | − | − | − | − | − | − | − | − | − | + | + | + |
| 3.13 | − | − | − | − | − | − | − | − | − | + | + | + |
| 0 | − | − | − | − | − | − | − | − | + | + | + | + |
| | | | | 90-397 (synergism) | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | − | + |
| 6.25 | − | − | − | − | − | − | − | − | − | − | + | + |
| 3.13 | − | − | − | − | − | − | − | − | − | + | + | + |
| 0 | − | − | − | − | − | − | − | − | + | + | + | + |

TABLE 10

| Oxethazaine | Compound (II) (µg/ml) | | | | | | | | | | | |
|---|---|---|---|---|---|---|---|---|---|---|---|---|
| (µg/ml) | 100 | 50 | 25 | 12.5 | 6.25 | 3.13 | 1.56 | 0.8 | 0.4 | 0.2 | 0.1 | 0 |
| | | | | 90-414(1) (additive effect) | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | − | + |
| 6.25 | − | − | − | − | − | − | − | − | − | + | + | + |
| 3.13 | − | − | − | − | − | − | − | − | − | + | + | + |
| 0 | − | − | − | − | − | − | − | − | + | + | + | + |
| | | | | 90-392 (synergism) | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | − | + |
| 6.25 | − | − | − | − | − | − | − | − | − | − | + | + |
| 3.13 | − | − | − | − | − | − | − | − | − | − | + | + |
| 0 | − | − | − | − | − | − | − | − | + | + | + | + |

Antimicrobial Activity Test 4

Anti-*H. pylori* Activity of Oxethazaine used in Combination with Compound (III)

1. Method

The effect of oxethazaine used in combination with compound (III) (omeprazole) was examined in the same manner as in antimicrobial activity test 1, using the checker board method.

2. Results

Hereinafter, the results are shown for each strain in the same manner as in antimicrobial activity test 3.

TABLE 11

| Oxethazaine | Compound (III) (µg/ml) | | | | | | |
|---|---|---|---|---|---|---|---|
| (µg/ml) | 100 | 50 | 25 | 12.5 | 6.25 | 3.13 | 0 |
| | NCTC 11637 (additive effect) | | | | | | |
| 100 | − | − | − | − | − | − | − |
| 50 | − | − | − | − | − | − | − |
| 25 | − | − | − | − | − | − | − |
| 12.5 | − | − | − | − | + | + | + |
| 6.25 | − | − | − | + | + | + | + |
| 3.13 | − | − | + | + | + | + | + |
| 0 | − | − | + | + | + | + | + |
| | NCTC 11639 (additive effect) | | | | | | |
| 100 | − | − | − | − | − | − | − |
| 50 | − | − | − | − | − | − | − |
| 25 | − | − | − | − | − | − | + |
| 12.5 | − | − | − | − | + | + | + |
| 6.25 | − | − | − | + | + | + | + |
| 3.13 | − | − | − | + | + | + | + |
| 0 | − | − | − | + | + | + | + |
| | NCTC 11916 (additive effect) | | | | | | |
| 100 | − | − | − | − | − | − | − |
| 50 | − | − | − | − | − | − | − |
| 25 | − | − | − | − | − | − | − |
| 12.5 | − | − | − | − | + | + | + |

TABLE 11-continued

| Oxethazaine | Compound (III) (μg/ml) | | | | | | |
|---|---|---|---|---|---|---|---|
| (μg/ml) | 100 | 50 | 25 | 12.5 | 6.25 | 3.13 | 0 |
| 6.25 | − | − | − | + | + | + | + |
| 3.13 | − | − | + | + | + | + | + |
| 0 | − | − | + | + | + | + | |

TABLE 12

| Oxethazaine | Compound (III) (μg/ml) | | | | | | |
|---|---|---|---|---|---|---|---|
| (μg/ml) | 100 | 50 | 25 | 12.5 | 6.25 | 3.13 | 0 |
| EH 12 (additive effect) | | | | | | | |
| 100 | − | − | − | − | − | − | − |
| 50 | − | − | − | − | − | − | − |
| 25 | − | − | − | − | − | − | − |
| 12.5 | − | − | − | − | − | + | + |
| 6.25 | − | − | − | − | + | + | + |
| 3.13 | − | − | − | + | + | + | + |
| 0 | − | − | − | + | + | + | |
| EH 13 (additive effect) | | | | | | | |
| 100 | − | − | − | − | − | − | − |
| 50 | − | − | − | − | − | − | − |
| 25 | − | − | − | − | − | − | − |
| 12.5 | − | − | − | − | − | − | + |
| 6.25 | − | − | − | − | + | + | + |
| 3.13 | − | − | − | − | + | + | + |
| 0 | − | − | − | + | + | + | |
| EH 16 (additive effect) | | | | | | | |
| 100 | − | − | − | − | − | − | − |
| 50 | − | − | − | − | − | − | − |
| 25 | − | − | − | − | − | − | − |
| 12.5 | − | − | − | − | + | + | + |
| 6.25 | − | − | − | + | + | + | + |
| 3.13 | − | − | − | + | + | + | + |
| 0 | − | − | − | + | + | + | |

TABLE 13

| Oxethazaine | Compound (III) (μg/ml) | | | | | | |
|---|---|---|---|---|---|---|---|
| (μg/ml) | 100 | 50 | 25 | 12.5 | 6.25 | 3.13 | 0 |
| EH 26 (additive effect) | | | | | | | |
| 100 | − | − | − | — | − | − | — |
| 50 | − | − | − | − | − | − | − |
| 25 | − | − | − | − | − | − | − |
| 12.5 | − | − | − | − | + | + | + |
| 6.25 | − | − | − | + | + | + | + |
| 3.13 | − | − | − | + | + | + | + |
| 0 | − | − | − | + | + | + | |
| 90-384 (additive effect) | | | | | | | |
| 100 | − | − | − | − | − | − | − |
| 50 | − | − | − | − | − | − | − |
| 25 | − | − | − | − | − | − | − |
| 12.5 | − | − | − | − | + | + | + |
| 6.25 | − | − | − | + | + | + | + |
| 3.13 | − | − | − | + | + | + | + |
| 0 | − | − | + | + | + | + | |
| 90-390 (additive effect) | | | | | | | |
| 100 | − | − | − | − | − | − | − |
| 50 | − | − | − | − | − | − | − |
| 25 | − | − | − | − | − | − | − |
| 12.5 | − | − | − | − | − | + | + |
| 6.25 | − | − | − | − | + | + | + |

TABLE 13-continued

| Oxethazaine | Compound (III) (μg/ml) | | | | | | |
|---|---|---|---|---|---|---|---|
| (μg/ml) | 100 | 50 | 25 | 12.5 | 6.25 | 3.13 | 0 |
| 3.13 | − | − | − | + | + | + | + |
| 0 | − | − | + | + | + | + | |

TABLE 14

| Oxethazaine | Compound (III) (μg/ml) | | | | | | |
|---|---|---|---|---|---|---|---|
| (μg/ml) | 100 | 50 | 25 | 12.5 | 6.25 | 3.13 | 0 |
| 89-357 (additive effect) | | | | | | | |
| 100 | − | − | − | − | − | − | − |
| 50 | − | − | − | − | − | − | − |
| 25 | − | − | − | − | − | − | − |
| 12.5 | − | − | − | − | + | + | + |
| 6.25 | − | − | − | + | + | + | + |
| 3.13 | − | − | + | + | + | + | + |
| 0 | − | − | + | + | + | + | |
| 90-428 (additive effect) | | | | | | | |
| 100 | − | − | − | − | − | − | − |
| 50 | − | − | − | − | − | − | − |
| 25 | − | − | − | − | − | − | − |
| 12.5 | − | − | − | − | + | + | + |
| 6.25 | − | − | − | + | + | + | + |
| 3.13 | − | − | + | + | + | + | + |
| 0 | − | − | + | + | + | + | |
| 89-360 (additive effect) | | | | | | | |
| 100 | − | − | − | − | − | − | − |
| 50 | − | − | − | − | − | − | − |
| 25 | − | − | − | − | − | − | − |
| 12.5 | − | − | − | − | + | + | + |
| 6.25 | − | − | − | + | + | + | + |
| 3.13 | − | − | + | + | + | + | + |
| 0 | − | − | + | + | + | + | |

TABLE 15

| Oxethazaine | Compound (III) (μg/ml) | | | | | | |
|---|---|---|---|---|---|---|---|
| (μg/ml) | 100 | 50 | 25 | 12.5 | 6.25 | 3.13 | 0 |
| 90-407 (additive effect) | | | | | | | |
| 100 | − | − | − | − | − | − | − |
| 50 | − | − | − | − | − | − | − |
| 25 | − | − | − | − | − | − | − |
| 12.5 | − | − | − | − | + | + | + |
| 6.25 | − | − | − | − | + | + | + |
| 3.13 | − | − | − | + | + | + | + |
| 0 | − | − | − | + | + | + | |
| 90-411 (additive effect) | | | | | | | |
| 100 | − | − | − | − | − | − | − |
| 50 | − | − | − | − | − | − | − |
| 25 | − | − | − | − | − | − | − |
| 12.5 | − | − | − | − | − | − | + |
| 6.25 | − | − | − | − | + | + | + |
| 3.13 | − | − | − | + | + | + | + |
| 0 | − | − | − | + | + | + | |
| 9-355 (additive effect) | | | | | | | |
| 100 | − | − | − | − | − | − | − |
| 50 | − | − | − | − | − | − | − |
| 25 | − | − | − | − | − | − | − |
| 12.5 | − | − | − | − | − | − | − |
| 6.25 | − | − | − | − | + | + | + |

TABLE 15-continued

| Oxethazaine | Compound (III) (μg/ml) | | | | | | |
|---|---|---|---|---|---|---|---|
| (μg/ml) | 100 | 50 | 25 | 12.5 | 6.25 | 3.13 | 0 |
| 3.13 | − | − | − | + | + | + | + |
| 0 | − | − | − | + | + | + | |

TABLE 16

| Oxethazaine | Compound (III) (μg/ml) | | | | | | |
|---|---|---|---|---|---|---|---|
| (μg/ml) | 100 | 50 | 25 | 12.5 | 6.25 | 3.13 | 0 |
| 90-397 (additive effect) | | | | | | | |
| 100 | − | − | − | − | − | − | − |
| 50 | − | − | − | − | − | − | − |
| 25 | − | − | − | − | − | − | − |
| 12.5 | − | − | − | + | + | + | + |
| 6.25 | − | − | − | + | + | + | + |
| 3.13 | − | − | − | + | + | + | + |
| 0 | − | − | − | + | + | + | |
| 90-388 (additive effect) | | | | | | | |
| 100 | − | − | − | − | − | − | − |
| 50 | − | − | − | − | − | − | − |
| 25 | − | − | − | − | − | − | − |
| 12.5 | − | − | − | + | + | + | |
| 6.25 | − | − | + | + | + | + | |
| 3.13 | − | − | − | + | + | + | + |
| 0 | − | − | + | + | + | + | |
| 90-388(1) (additive effect) | | | | | | | |
| 100 | − | − | − | − | − | − | − |
| 50 | − | − | − | − | − | − | − |
| 25 | − | − | − | − | − | − | − |
| 12.5 | − | − | − | − | + | + | |
| 6.25 | − | − | − | + | + | + | |
| 3.13 | − | − | − | + | + | + | + |
| 0 | − | − | − | + | + | + | |

TABLE 17

| Oxethazaine | Compound (III) (μg/ml) | | | | | | |
|---|---|---|---|---|---|---|---|
| (μg/ml) | 100 | 50 | 25 | 12.5 | 6.25 | 3.13 | 0 |
| 90-390(1) (additive effect) | | | | | | | |
| 100 | − | − | − | − | − | − | − |
| 50 | − | − | − | − | − | − | − |
| 25 | − | − | − | − | − | − | − |
| 12.5 | − | − | − | − | + | + | + |
| 6.25 | − | − | − | − | + | + | + |
| 3.13 | − | − | − | + | + | + | + |
| 0 | − | − | − | + | + | + | |
| 90-414 (synergism) | | | | | | | |
| 100 | − | − | − | − | − | − | − |
| 50 | − | − | − | − | − | − | − |

TABLE 17-continued

| Oxethazaine | Compound (III) (μg/ml) | | | | | | |
|---|---|---|---|---|---|---|---|
| (μg/ml) | 100 | 50 | 25 | 12.5 | 6.25 | 3.13 | 0 |
| 25 | − | − | − | − | − | − | − |
| 12.5 | − | − | − | − | − | + | + |
| 6.25 | − | − | − | − | + | + | + |
| 3.13 | − | − | − | + | + | + | + |
| 0 | − | − | + | + | + | + | |
| 90-397 (additive effect) | | | | | | | |
| 100 | − | − | − | − | − | − | − |
| 50 | − | − | − | − | − | − | − |
| 25 | − | − | − | − | − | − | − |
| 12.5 | − | − | − | − | − | + | + |
| 6.25 | − | − | − | − | + | + | + |
| 3.13 | − | − | − | − | + | + | + |
| 0 | − | − | − | + | + | + | |

TABLE 18

| Oxethazaine | Compound (III) (μg/ml) | | | | | | |
|---|---|---|---|---|---|---|---|
| (μg/ml) | 100 | 50 | 25 | 12.5 | 6.25 | 3.13 | 0 |
| 90-414(1) (additive effect) | | | | | | | |
| 100 | − | − | − | − | − | − | − |
| 50 | − | − | − | − | − | − | − |
| 25 | − | − | − | − | − | − | − |
| 12.5 | − | − | − | − | − | + | + |
| 6.25 | − | − | − | − | + | + | + |
| 3.13 | − | − | − | − | + | + | + |
| 0 | − | − | − | + | + | + | |
| 90-392 (additive effect) | | | | | | | |
| 100 | − | − | − | − | − | − | − |
| 50 | − | − | − | − | − | − | − |
| 25 | − | − | − | − | − | − | − |
| 12.5 | − | − | − | − | + | + | + |
| 6.25 | − | − | − | − | + | + | + |
| 3.13 | − | − | − | − | + | + | + |
| 0 | − | − | − | + | + | + | |

Antimicrobial Activity Test 5

Anti-*H. pylori* Activity of Oxethazaine used in Combination with Combination (IV)

1. Method

The effect of oxethazaine used in combination with compound (IV) (lansoprazole) was examined in the same manner as in antimicrobial activity test 1, using the checker board method.

2. Results

Hereinafter, the results are shown for each strain in the same manner as in antimicrobial activity test 3.

TABLE 19

| Oxethazaine | Compound (IV) (μg/ml) | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| NCTC 11637 (additive effect) | | | | | | | | | | | | |
| 100 | − | − | − | − | − | − | − | − | − | − | − | − |
| 50 | − | − | − | − | − | − | − | − | − | − | − | − |

TABLE 19-continued

| Oxethazaine (μg/ml) | Compound (IV) (μg/ml) | | | | | | | | | | | |
|---|---|---|---|---|---|---|---|---|---|---|---|---|
| | 100 | 50 | 25 | 12.5 | 6.25 | 3.13 | 1.56 | 0.8 | 0.4 | 0.2 | 0.1 | 0 |
| 25 | − | − | − | − | − | − | − | − | − | − | − | − |
| 12.5 | − | − | − | − | − | − | + | + | + | + | + | + |
| 6.25 | − | − | − | − | + | + | + | + | + | + | + | + |
| 3.13 | − | − | − | − | + | + | + | + | + | + | + | + |
| 0 | − | − | − | − | + | + | + | + | + | + | + |  |
| NCTC 11639 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | + | + | + | + | + | + |
| 6.25 | − | − | − | − | − | + | + | + | + | + | + | + |
| 3.13 | − | − | − | − | − | + | + | + | + | + | + | + |
| 0 | − | − | − | − | − | + | + | + | + | + | + |  |
| NCTC 11916 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | + | + | + | + | + | + |
| 6.25 | − | − | − | − | − | + | + | + | + | + | + | + |
| 3.13 | − | − | − | − | + | + | + | + | + | + | + | + |
| 0 | − | − | − | − | − | + | + | + | + | + | + |  |

TABLE 20

| Oxethazaine (μg/ml) | Compound (IV) (μg/ml) | | | | | | | | | | | |
|---|---|---|---|---|---|---|---|---|---|---|---|---|
| | 100 | 50 | 25 | 12.5 | 6.25 | 3.13 | 1.56 | 0.8 | 0.4 | 0.2 | 0.1 | 0 |
| EH 12 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | + | + | + | + | + |
| 6.25 | − | − | − | − | − | − | + | + | + | + | + | + |
| 3.13 | − | − | − | − | − | − | + | + | + | + | + | + |
| 0 | − | − | − | − | − | − | + | + | + | + | + |  |
| EH 13 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | + | + | + | + | + |
| 6.25 | − | − | − | − | − | − | + | + | + | + | + | + |
| 3.13 | − | − | − | − | − | − | + | + | + | + | + | + |
| 0 | − | − | − | − | − | + | + | + | + | + | + |  |
| EH 16 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | + | + | + | + | + |
| 6.25 | − | − | − | − | − | − | + | + | + | + | + | + |
| 3.13 | − | − | − | − | − | + | + | + | + | + | + | + |
| 0 | − | − | − | − | − | + | + | + | + | + | + |  |

TABLE 21

| Oxethazaine (μg/ml) | Compound (IV) (μg/ml) | | | | | | | | | | | |
|---|---|---|---|---|---|---|---|---|---|---|---|---|
| | 100 | 50 | 25 | 12.5 | 6.25 | 3.13 | 1.56 | 0.8 | 0.4 | 0.2 | 0.1 | 0 |
| EH 26 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | + | + | + | + |

TABLE 21-continued

| Oxethazaine | Compound (IV) (μg/ml) | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| 6.25 | − | − | − | − | − | − | + | + | + | + | + | + |
| 3.13 | − | − | − | − | − | − | + | + | + | + | + | + |
| 0 | − | − | − | − | − | + | + | + | + | + | + | |
| 90-384 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | + | + | + | + | + |
| 6.25 | − | − | − | − | − | − | + | + | + | + | + | + |
| 3.13 | − | − | − | − | − | − | + | + | + | + | + | + |
| 0 | − | − | − | − | − | − | + | + | + | + | + | |
| 90-390 (synergism) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | + | + | + |
| 12.5 | − | − | − | − | − | − | − | − | + | + | + | + |
| 6.25 | − | − | − | − | − | − | + | + | + | + | + | + |
| 3.13 | − | − | − | − | − | − | + | + | + | + | + | + |
| 0 | − | − | − | − | − | − | + | + | + | + | + | |

TABLE 22

| Oxethazaine | Compound (IV) (μg/ml) | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| 89-357 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | + | + | + | + |
| 6.25 | − | − | − | − | − | − | − | + | + | + | + | + |
| 3.13 | − | − | − | − | − | − | + | + | + | + | + | + |
| 0 | − | − | − | − | − | − | + | + | + | + | + | |
| 90-428 (synergism) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | + | + | + |
| 12.5 | − | − | − | − | − | − | − | + | + | + | + | + |
| 6.25 | − | − | − | − | − | − | + | + | + | + | + | + |
| 3.13 | − | − | − | − | − | − | + | + | + | + | + | + |
| 0 | − | − | − | − | − | + | + | + | + | + | + | |
| 89-360 (synergism) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | + | + | + |
| 12.5 | − | − | − | − | − | − | − | + | + | + | + | + |
| 6.25 | − | − | − | − | − | − | + | + | + | + | + | + |
| 3.13 | − | − | − | − | − | + | + | + | + | + | + | + |
| 0 | − | − | − | − | − | + | + | + | + | + | + | |

TABLE 23

| Oxethazaine | Compound (IV) (μg/ml) | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| 89-360(1) (synergism) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | + | + | + |
| 12.5 | − | − | − | − | − | − | − | − | + | + | + | + |
| 6.25 | − | − | − | − | − | − | + | + | + | + | + | + |

TABLE 23-continued

| Oxethazaine | Compound (IV) (μg/ml) | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| 3.13 | − | − | − | − | − | + | + | + | + | + | + | + |
| 0 | − | − | − | − | − | − | + | + | + | + | + | + |
| 90-407 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | + |
| 6.25 | − | − | − | − | − | − | − | + | + | + | + | + |
| 3.13 | − | − | − | − | − | − | + | + | + | + | + | + |
| 0 | − | − | − | − | − | − | + | + | + | + | + | |
| 90-411 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | − | + | + |
| 6.25 | − | − | − | − | − | − | − | + | + | + | + | + |
| 3.13 | − | − | − | − | − | − | + | + | + | + | + | + |
| 0 | − | − | − | − | − | − | + | + | + | + | + | |

TABLE 24

| Oxethazaine | Compound (IV) (μg/ml) | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| 89-355 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | + | + | + | + | + |
| 6.25 | − | − | − | − | − | − | + | + | + | + | + | + |
| 3.13 | − | − | − | − | − | − | + | + | + | + | + | + |
| 0 | − | − | − | − | − | − | + | + | + | + | + | |
| 90-397 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | + | + | + |
| 12.5 | − | − | − | − | − | − | − | + | + | + | + | + |
| 6.25 | − | − | − | − | − | − | + | + | + | + | + | + |
| 3.13 | − | − | − | − | − | − | + | + | + | + | + | + |
| 0 | − | − | − | − | − | − | + | + | + | + | + | |
| 90-388 (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | + | + |
| 12.5 | − | − | − | − | − | − | + | + | + | + | + | + |
| 6.25 | − | − | − | − | − | − | + | + | + | + | + | + |
| 3.13 | − | − | − | − | − | − | + | + | + | + | + | + |
| 0 | − | − | − | − | − | − | + | + | + | + | + | |

TABLE 25

| Oxethazaine | Compound (IV) (μg/ml) | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| 90-407(1) (additive effect) | | | | | | | | | | | | |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | + | + | + | + |
| 6.25 | − | − | − | − | − | − | + | + | + | + | + | + |
| 3.13 | − | − | − | − | − | − | + | + | + | + | + | + |
| 0 | − | − | − | − | − | + | + | + | + | + | + | |

TABLE 25-continued

| Oxethazaine | Compound (IV) (μg/ml) | | | | | | | | | | |
|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |

90-388(1) (synergism)

| Oxethazaine (μg/ml) | 100 | 50 | 25 | 12.5 | 6.25 | 3.13 | 1.56 | 0.8 | 0.4 | 0.2 | 0.1 | 0 |
|---|---|---|---|---|---|---|---|---|---|---|---|---|
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | + | + | + | + |
| 6.25 | − | − | − | − | − | − | − | + | + | + | + | + |
| 3.13 | − | − | − | − | − | − | + | + | + | + | + | + |
| 0 | − | − | − | − | − | + | + | + | + | + | + |   |

90-390(1) (synergism)

| Oxethazaine (μg/ml) | 100 | 50 | 25 | 12.5 | 6.25 | 3.13 | 1.56 | 0.8 | 0.4 | 0.2 | 0.1 | 0 |
|---|---|---|---|---|---|---|---|---|---|---|---|---|
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | − | + | + | + |
| 6.25 | − | − | − | − | − | − | − | + | + | + | + | + |
| 3.13 | − | − | − | − | − | − | + | + | + | + | + | + |
| 0 | − | − | − | − | − | + | + | + | + | + | + |   |

TABLE 26

| Oxethazaine | Compound (IV) (μg/ml) | | | | | | | | | | |
|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |

90-414 (synergism)

| Oxethazaine (μg/ml) | 100 | 50 | 25 | 12.5 | 6.25 | 3.13 | 1.56 | 0.8 | 0.4 | 0.2 | 0.1 | 0 |
|---|---|---|---|---|---|---|---|---|---|---|---|---|
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | + | + | + | + |
| 625 | − | − | − | − | − | − | + | + | + | + | + | + |
| 3.13 | − | − | − | − | − | − | + | + | + | + | + | + |
| 0 | − | − | − | − | − | + | + | + | + | + | + |   |

90-397 (synergism)

| Oxethazaine (μg/ml) | 100 | 50 | 25 | 12.5 | 6.25 | 3.13 | 1.56 | 0.8 | 0.4 | 0.2 | 0.1 | 0 |
|---|---|---|---|---|---|---|---|---|---|---|---|---|
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | + | + | + | + |
| 6.25 | − | − | − | − | − | − | + | + | + | + | + | + |
| 3.13 | − | − | − | − | − | − | + | + | + | + | + | + |
| 0 | − | − | − | − | − | + | + | + | + | + | + |   |

90-414(1) (synergism)

| Oxethazaine (μg/ml) | 100 | 50 | 25 | 12.5 | 6.25 | 3.13 | 1.56 | 0.8 | 0.4 | 0.2 | 0.1 | 0 |
|---|---|---|---|---|---|---|---|---|---|---|---|---|
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | − | − | + | + | + | + |
| 6.25 | − | − | − | − | − | − | − | + | + | + | + | + |
| 3.13 | − | − | − | − | − | − | + | + | + | + | + | + |
| 0 | − | − | − | − | − | + | + | + | + | + | + |   |

TABLE 27

90-392 (additive effect)

| Oxethazaine | Compound (IV) (μg/ml) | | | | | | | | | | |
|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0 |
| 100 | − | − | − | − | − | − | − | − | − | − | − | − |
| 50 | − | − | − | − | − | − | − | − | − | − | − | − |
| 25 | − | − | − | − | − | − | − | − | − | − | − | − |
| 12.5 | − | − | − | − | − | − | + | + | + | + | + | + |
| 6.25 | − | − | − | − | − | + | + | + | + | + | + | + |
| 3.13 | − | − | − | − | − | + | + | + | + | + | + | + |
| 0 | − | − | − | − | − | + | + | + | + | + | + |   |

As is evident from the results of antimicrobial activity tests 3 to 4 mentioned above, further synergism and additive effect for anti-*H. pylori* activity were recognized when oxethazaine was used in combination with PPI.

The results are shown in the following Table.

|  | Compound | | |
| --- | --- | --- | --- |
|  | (II) | (III) | (IV) |
| synergism | 5 strains/<br>25 strains | 1 strains/<br>23 strains | 10 strains/<br>25 strains |
| additive effect | 20 strains/<br>25 strains | 22 strains/<br>23 strains | 15 strains/<br>25 strains |

From these results, the further excellent *H. pylori*-eradicating effect of the present invention comprising combined use of oxethazaine and PPI is evident, and the dose of PPI administered can also be reduced when both the compounds are used in combination.

Antimicrobial Activity Test 6

Anti-*H. pylori* Activity of Oxethazaine used in Combination with an Antibiotic

1. Method

The effect of combined use with amoxicillin (AMPC), clarithromycin (CAM) or roxithromycin (RXM) was examined in the same manner as in antimicrobial activity test 1, using the checker board method.

2. Results

Hereinafter, the results are shown for each strain in the same manner as in antimicrobial activity test 3.

1) Amoxicillin (AMPC)

TABLE 28

| Oxethazaine | AMPC ($\mu$g/ml) | | | | | | | | | | | | | | | |
| --- | --- | --- | --- | --- | --- | --- | --- | --- | --- | --- | --- | --- | --- | --- | --- | --- |
| ($\mu$g/ml) | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| NCTC11637 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | + | + |
| 6.25 | − | − | − | − | − | − | − | − | − | − | − | − | − | + | + | + |
| 3.13 | − | − | − | − | − | − | − | − | − | − | − | − | − | + | + | + |
| 0 | − | − | − | − | − | − | − | − | − | − | − | − | − | + | + |  |
| NCTC11639 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | + | + |
| 6.25 | − | − | − | − | − | − | − | − | − | − | − | − | − | − | + | + |
| 3.13 | − | − | − | − | − | − | − | − | − | − | − | − | − | − | + | + |
| 0 | − | − | − | − | − | − | − | − | − | − | − | − | − | − | + | + |

TABLE 29

| Oxethazaine | AMPC ($\mu$g/ml) | | | | | | | | | | | | | | | |
| --- | --- | --- | --- | --- | --- | --- | --- | --- | --- | --- | --- | --- | --- | --- | --- | --- |
| ($\mu$g/ml) | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| NCTC11916 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | + | + |
| 6.25 | − | − | − | − | − | − | − | − | − | − | − | − | − | + | + | + |
| 3.13 | − | − | − | − | − | − | − | − | − | − | − | − | − | + | + | + |
| 0 | − | − | − | − | − | − | − | − | − | − | − | − | − | + | + |  |
| NCTC49503 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | + | + |
| 6.25 | − | − | − | − | − | − | − | − | − | − | − | − | − | + | + | + |
| 3.13 | − | − | − | − | − | − | − | − | − | − | − | − | − | + | + | + |
| 0 | − | − | − | − | − | − | − | − | − | − | − | − | − | + | + |  |

TABLE 30

| Oxethazaine (μg/ml) | AMPC (μg/ml) | | | | | | | | | | | | | | | |
|---|---|---|---|---|---|---|---|---|---|---|---|---|---|---|---|---|
| | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| EH 13 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | − | + |
| 6.25 | − | − | − | − | − | − | − | − | − | − | − | − | − | − | − | + |
| 3.13 | − | − | − | − | − | − | − | − | − | − | − | − | − | + | + | + |
| 0 | − | − | − | − | − | − | − | − | − | − | − | − | − | − | + | + |
| EH 16 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | + | + |
| 6.25 | − | − | − | − | − | − | − | − | − | − | − | − | − | − | + | + |
| 3.13 | − | − | − | − | − | − | − | − | − | − | − | − | − | − | + | + |
| 0 | − | − | − | − | − | − | − | − | − | − | − | − | − | − | − | + |

TABLE 31

| Oxethazaine (μg/ml) | AMPC (μg/ml) | | | | | | | | | | | | | | | |
|---|---|---|---|---|---|---|---|---|---|---|---|---|---|---|---|---|
| | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| EH 26 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | − | + |
| 6.25 | − | − | − | − | − | − | − | − | − | − | − | − | − | − | − | + |
| 3.13 | − | − | − | − | − | − | − | − | − | − | − | − | − | − | − | + |
| 0 | − | − | − | − | − | − | − | − | − | − | − | − | − | − | + | |
| 89-357 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | + | + |
| 6.25 | − | − | − | − | − | − | − | − | − | − | − | − | − | + | + | + |
| 3.13 | − | − | − | − | − | − | − | − | − | − | − | − | − | + | + | + |
| 0 | − | − | − | − | − | − | − | − | − | − | − | − | − | + | + | |

TABLE 32

| Oxethazaine (μg/ml) | AMPC (μg/ml) | | | | | | | | | | | | | | | |
|---|---|---|---|---|---|---|---|---|---|---|---|---|---|---|---|---|
| | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| 90-388 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | + | + |
| 6.25 | − | − | − | − | − | − | − | − | − | − | − | − | − | + | + | + |
| 3.13 | − | − | − | − | − | − | − | − | − | − | − | − | − | + | + | + |
| 0 | − | − | − | − | − | − | − | − | − | − | − | − | − | + | + | |
| 90-390 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | + | + |
| 6.25 | − | − | − | − | − | − | − | − | − | − | − | − | − | − | + | + |
| 3.13 | − | − | − | − | − | − | − | − | − | − | − | − | − | − | + | + |
| 0 | − | − | − | − | − | − | − | − | − | − | − | − | − | + | + | |

TABLE 33

| Oxethazaine (μg/ml) | AMPC (μg/ml) | | | | | | | | | | | | | | | |
|---|---|---|---|---|---|---|---|---|---|---|---|---|---|---|---|---|
| | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| 90-392 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | + | + |
| 6.25 | − | − | − | − | − | − | − | − | − | − | − | − | − | + | + | + |
| 3.13 | − | − | − | − | − | − | − | − | − | − | − | − | + | + | + | + |
| 0 | − | − | − | − | − | − | − | − | − | − | − | − | + | + | + | |
| 90-397 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | + | + | + | + |
| 6.25 | − | − | − | − | − | − | − | − | − | − | − | − | + | + | + | + |
| 3.13 | − | − | − | − | − | − | − | − | − | − | − | + | + | + | + | + |
| 0 | − | − | − | − | − | − | − | − | − | − | − | + | + | + | + | |

TABLE 34

| Oxethazaine (μg/ml) | AMPC (μg/ml) | | | | | | | | | | | | | | | |
|---|---|---|---|---|---|---|---|---|---|---|---|---|---|---|---|---|
| | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| 90-407 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | + | + | + |
| 6.25 | − | − | − | − | − | − | − | − | − | − | − | − | + | + | + | + |
| 3.13 | − | − | − | − | − | − | − | − | − | − | − | − | + | + | + | + |
| 0 | − | − | − | − | − | − | − | − | − | − | − | − | + | + | + | |
| 90-414 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | + | + | + | + | + |
| 6.25 | − | − | − | − | − | − | − | − | − | − | − | + | + | + | + | + |
| 3.13 | − | − | − | − | − | − | − | − | − | − | − | + | + | + | + | + |
| 0 | − | − | − | − | − | − | − | − | − | − | + | + | + | + | + | |

TABLE 35

| Oxethazaine (μg/ml) | AMPC (μg/ml) | | | | | | | | | | | | | | | |
|---|---|---|---|---|---|---|---|---|---|---|---|---|---|---|---|---|
| | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| 90-428 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | + | + | + |
| 6.25 | − | − | − | − | − | − | − | − | − | − | − | − | + | + | + | + |
| 3.13 | − | − | − | − | − | − | − | − | − | − | − | − | + | + | + | + |
| 0 | − | − | − | − | − | − | − | − | − | − | − | − | + | + | + | |

2) clarithromycin (CAM)

TABLE 36

| Oxethazaine | CAM (μg/ml) | | | | | | | | | | | | | | | |
|---|---|---|---|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| | | | | | NCTC11637 (additive effect) | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | − | − |
| 6.25 | − | − | − | − | − | − | − | − | − | − | − | − | − | − | + | + |
| 3.13 | − | − | − | − | − | − | − | − | − | − | − | − | − | + | + | + |
| 0 | − | − | − | − | − | − | − | − | − | − | − | − | + | + | + | |
| | | | | | NCTC11639 (additive effect) | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | + | + | + |
| 6.25 | − | − | − | − | − | − | − | − | − | − | − | − | + | + | + | + |
| 3.13 | − | − | − | − | − | − | − | − | − | − | − | − | − | + | + | + |
| 0 | − | − | − | − | − | − | − | − | − | − | + | + | + | + | | |

TABLE 37

| Oxethazaine | CAM (μg/ml) | | | | | | | | | | | | | | | |
|---|---|---|---|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| | | | | | NCTC11916 (synergism) | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | − | − |
| 6.25 | − | − | − | − | − | − | − | − | − | − | − | − | − | − | + | + |
| 3.13 | − | − | − | − | − | − | − | − | − | − | − | − | − | + | + | + |
| 0 | − | − | − | − | − | − | − | − | − | − | − | − | + | + | + | |
| | | | | | ATCC49503 (additive effect) | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | − | + |
| 6.25 | − | − | − | − | − | − | − | − | − | − | − | − | − | − | + | + |
| 3.13 | − | − | − | − | − | − | − | − | − | − | − | − | − | − | + | + |
| 0 | − | − | − | − | − | − | − | − | − | − | − | − | − | + | + | |

TABLE 38

| Oxethazaine | CAM (μg/ml) | | | | | | | | | | | | | | | |
|---|---|---|---|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| | | | | | EH 12 (synergism) | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | − | − |
| 6.25 | − | − | − | − | − | − | − | − | − | − | − | − | − | − | + | + |
| 3.13 | − | − | − | − | − | − | − | − | − | − | − | − | − | − | + | + |
| 0 | − | − | − | − | − | − | − | − | − | − | − | − | + | + | + | |
| | | | | | EH 13 (additive effect) | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | − | + |
| 6.25 | − | − | − | − | − | − | − | − | − | − | − | − | − | − | + | + |

TABLE 38-continued

| Oxethazaine | CAM (μg/ml) | | | | | | | | | | | | | | |
|---|---|---|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| 3.13 | − | − | − | − | − | − | − | − | − | − | − | − | − | − | + | + |
| 0 | − | − | − | − | − | − | − | − | − | − | − | − | − | + | + |

TABLE 39

| Oxethazaine | CAM (μg/ml) | | | | | | | | | | | | | | | |
|---|---|---|---|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| EH 16 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | − | + |
| 6.25 | − | − | − | − | − | − | − | − | − | − | − | − | − | + | + | + |
| 3.13 | − | − | − | − | − | − | − | − | − | − | − | − | + | + | + | + |
| 0 | − | − | − | − | − | − | − | − | − | − | − | − | + | + | + |
| EH 26 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | + | + |
| 6.25 | − | − | − | − | − | − | − | − | − | − | − | − | − | + | + | + |
| 3.13 | − | − | − | − | − | − | − | − | − | − | − | − | + | + | + | + |
| 0 | − | − | − | − | − | − | − | − | − | − | − | − | + | + | + |

TABLE 40

| Oxethazaine | CAM (μg/ml) | | | | | | | | | | | | | | | |
|---|---|---|---|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| 89-355 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | − | − |
| 6.25 | − | − | − | − | − | − | − | − | − | − | − | − | − | + | + | + |
| 3.13 | − | − | − | − | − | − | − | − | − | − | − | − | + | + | + | + |
| 0 | − | − | − | − | − | − | − | − | − | − | − | + | + | + | + |
| 89-357 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | − | + |
| 6.25 | − | − | − | − | − | − | − | − | − | − | − | − | − | + | + | + |
| 3.13 | − | − | − | − | − | − | − | − | − | − | − | − | − | + | + | + |
| 0 | − | − | − | − | − | − | − | − | − | − | − | − | + | + | + |

TABLE 41

| Oxethazaine | CAM (μg/ml) | | | | | | | | | | | | | | | |
|---|---|---|---|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| 90-360 (additive effect) | | | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | + |
| 12.5 | − | − | − | − | − | − | − | − | − | − | − | − | − | + | + | + |
| 6.25 | − | − | − | − | − | − | − | − | − | − | − | − | + | + | + | + |
| 3.13 | − | − | − | − | − | − | − | − | − | − | − | − | + | + | + | + |
| 0 | − | − | − | − | − | − | − | − | − | − | − | − | + | + | + |

TABLE 41-continued

| Oxethazaine | CAM (µg/ml) | | | | | | | | | | | | | | |
|---|---|---|---|---|---|---|---|---|---|---|---|---|---|---|---|
| (µg/ml) | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| | 90-384 (additive effect) | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | − | − |
| 6.25 | − | − | − | − | − | − | − | − | − | − | − | − | − | − | + | + | + |
| 3.13 | − | − | − | − | − | − | − | − | − | − | − | − | − | + | + | + | + |
| 0 | − | − | − | − | − | − | − | − | − | − | − | − | + | + | + | + |

TABLE 42

| Oxethazaine | CAM (µg/ml) | | | | | | | | | | | | | | |
|---|---|---|---|---|---|---|---|---|---|---|---|---|---|---|---|
| (µg/ml) | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| | 90-388 (additive effect) | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | + | + |
| 6.25 | − | − | − | − | − | − | − | − | − | − | − | − | + | + | + | + |
| 3.13 | − | − | − | − | − | − | − | − | − | − | − | − | + | + | + | + |
| 0 | − | − | − | − | − | − | − | − | − | − | − | + | + | + | + |
| | 90-390 (additive effect) | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | + | + |
| 6.25 | − | − | − | − | − | − | − | − | − | − | − | − | + | + | + | + |
| 3.13 | − | − | − | − | − | − | − | − | − | − | − | − | + | + | + | + |
| 0 | − | − | − | − | − | − | − | − | − | − | − | + | + | + | + |

TABLE 43

| Oxethazaine | CAM (µg/ml) | | | | | | | | | | | | | | |
|---|---|---|---|---|---|---|---|---|---|---|---|---|---|---|---|
| (µg/ml) | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| | 90-392 (additive effect) | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | − | − |
| 6.25 | − | − | − | − | − | − | − | − | − | − | − | − | − | + | + | + |
| 3.13 | − | − | − | − | − | − | − | − | − | − | − | − | − | + | + | + |
| 0 | − | − | − | − | − | − | − | − | − | − | − | − | + | + | + | + |
| | 90-394 (additive effect) | | | | | | | | | | | | | | |
| 100 | − | − | − | − | − | − | − | − | − | − | − | − | − | − | − | − |
| 50 | − | − | − | − | − | − | − | − | − | − | − | − | − | − | − | − |
| 25 | − | − | − | − | − | − | − | − | − | − | − | − | − | − | − | − |
| 12.5 | − | − | − | − | − | − | − | − | − | − | − | − | − | − | − | + |
| 6.25 | − | − | − | − | − | − | − | − | − | − | − | − | − | + | + | + |
| 3.13 | − | − | − | − | − | − | − | − | − | − | − | − | + | + | + | + |
| 0 | − | − | − | − | − | − | − | − | − | − | − | − | + | + | + | + |

TABLE 44

| Oxethazaine (μg/ml) | \multicolumn{16}{c}{CAM (μg/ml)} |
|---|---|---|---|---|---|---|---|---|---|---|---|---|---|---|---|---|
| | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| 90-397 (synergism) | | | | | | | | | | | | | | | | |
| 100 | – | – | – | – | – | – | – | – | – | – | – | – | – | – | – | – |
| 50 | – | – | – | – | – | – | – | – | – | – | – | – | – | – | – | – |
| 25 | – | – | – | – | – | – | – | – | – | – | – | – | – | – | – | – |
| 12.5 | – | – | – | – | – | – | – | – | – | – | – | – | – | – | – | + |
| 6.25 | – | – | – | – | – | – | – | – | – | – | – | + | + | + | + | + |
| 3.13 | – | – | – | – | – | – | – | – | – | – | – | + | + | + | + | + |
| 0 | – | – | – | – | – | – | – | – | + | + | + | + | + | + | + | + |
| 90-407 (additive effect) | | | | | | | | | | | | | | | | |
| 100 | – | – | – | – | – | – | – | – | – | – | – | – | – | – | – | – |
| 50 | – | – | – | – | – | – | – | – | – | – | – | – | – | – | – | – |
| 25 | – | – | – | – | – | – | – | – | – | – | – | – | – | – | – | – |
| 12.5 | – | – | – | – | – | – | – | – | – | – | – | – | – | – | + | + |
| 6.25 | – | – | – | – | – | – | – | – | – | – | – | – | – | + | + | + |
| 3.13 | – | – | – | – | – | – | – | – | – | – | – | – | – | + | + | + |
| 0 | – | – | – | – | – | – | – | – | – | – | – | + | + | + | + | + |

TABLE 45

| Oxethazaine (μg/ml) | \multicolumn{16}{c}{CAM (μg/ml)} |
|---|---|---|---|---|---|---|---|---|---|---|---|---|---|---|---|---|
| | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| 90-411 (synergism) | | | | | | | | | | | | | | | | |
| 100 | – | – | – | – | – | – | – | – | – | – | – | – | – | – | – | – |
| 50 | – | – | – | – | – | – | – | – | – | – | – | – | – | – | – | – |
| 25 | – | – | – | – | – | – | – | – | – | – | – | – | – | – | – | – |
| 12.5 | – | – | – | – | – | – | – | – | – | – | – | – | – | – | – | + |
| 6.25 | – | – | – | – | – | – | – | – | – | – | – | – | – | – | + | + |
| 3.13 | – | – | – | – | – | – | – | – | – | – | – | – | – | + | + | + |
| 0 | – | – | – | – | – | – | – | – | – | – | – | – | + | + | + | + |
| 90-414 (additive effect) | | | | | | | | | | | | | | | | |
| 100 | – | – | – | – | – | – | – | – | – | – | – | – | – | – | – | – |
| 50 | – | – | – | – | – | – | – | – | – | – | – | – | – | – | – | – |
| 25 | – | – | – | – | – | – | – | – | – | – | – | – | – | – | – | – |
| 12.5 | – | – | – | – | – | – | – | – | – | – | – | – | – | – | – | + |
| 6.25 | – | – | – | – | – | – | – | – | – | – | – | – | – | + | + | + |
| 3.13 | – | – | – | – | – | – | – | – | – | – | – | – | – | + | + | + |
| 0 | – | – | – | – | – | – | – | – | – | – | – | – | + | + | + | + |

TABLE 46

90-428 (synergism)

| Oxethazaine (μg/ml) | \multicolumn{16}{c}{CAM (μg/ml)} |
|---|---|---|---|---|---|---|---|---|---|---|---|---|---|---|---|---|
| | 100 | 50 | 25 | 12.5 | 6.25 | 3.13 | 1.56 | 0.8 | 0.4 | 0.2 | 0.1 | 0.05 | 0.024 | 0.012 | 0.006 | 0 |
| 100 | – | – | – | – | – | – | – | – | – | – | – | – | – | – | – | – |
| 50 | – | – | – | – | – | – | – | – | – | – | – | – | – | – | – | – |
| 25 | – | – | – | – | – | – | – | – | – | – | – | – | – | – | – | – |
| 12.5 | – | – | – | – | – | – | – | – | – | – | – | – | – | + | + | + |
| 6.25 | – | – | – | – | – | – | – | – | – | – | – | – | – | + | + | + |
| 3.13 | – | – | – | – | – | – | – | – | – | – | – | – | + | + | + | + |
| 0 | – | – | – | – | – | – | – | – | – | – | – | + | + | + | + | + |

3) Roxothromycin (RXM)

TABLE 47

| Oxethazaine | RXM (μg/ml) | | | | | | | | | | | | |
|---|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0 |
| NCTC11637 (additive effect) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | − | − |
| 6.25 | − | − | − | − | − | − | − | − | − | − | − | + | + |
| 3.13 | − | − | − | − | − | − | − | − | − | − | − | + | + |
| 0 | − | − | − | − | − | − | − | − | − | − | + | + | + |
| NCTC11639 (additive effect) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | + | + |
| 6.25 | − | − | − | − | − | − | − | − | − | + | + | + | + |
| 3.13 | − | − | − | − | − | − | − | − | − | + | + | + | + |
| 0 | − | − | − | − | − | − | − | − | + | + | + | + | + |

TABLE 48

| Oxethazaine | RXM (μg/ml) | | | | | | | | | | | | |
|---|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0 |
| NCTC11916 (additive effect) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | + |
| 12.5 | − | − | − | − | − | − | − | − | − | − | − | − | + |
| 6.25 | − | − | − | − | − | − | − | − | − | − | − | + | + |
| 3.13 | − | − | − | − | − | − | − | − | − | − | + | + | |
| 0 | | | | | | | | | | | | | |
| ATCC49503 (additive effect) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | − | + |
| 6.25 | − | − | − | − | − | − | − | − | − | − | − | − | + |
| 3.13 | − | − | − | − | − | − | − | − | − | − | − | − | + |
| 0 | − | − | − | − | − | − | − | − | − | − | − | + | |

TABLE 49

| Oxethazaine | RXM (μg/ml) | | | | | | | | | | | | |
|---|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0 |
| EH 12 (additive effect) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | − | − |
| 6.25 | − | − | − | − | − | − | − | − | − | − | − | + | + |
| 3.13 | − | − | − | − | − | − | − | − | − | − | − | + | + |
| 0 | − | − | − | − | − | − | − | − | − | − | + | + | |
| EH 13 (additive effect) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | − | + |
| 6.25 | − | − | − | − | − | − | − | − | − | − | − | + | + |

TABLE 49-continued

| Oxethazaine | RXM (μg/ml) | | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0 |
| 3.13 | − | − | − | − | − | − | − | − | − | − | − | + | + |
| 0 | − | − | − | − | − | − | − | − | − | − | + | + | |

TABLE 50

| Oxethazaine | RXM (μg/ml) | | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0 |
| EH 16 (synergism) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | − | + |
| 6.25 | − | − | − | − | − | − | − | − | − | − | − | + | + |
| 3.13 | − | − | − | − | − | − | − | − | − | + | + | + | + |
| 0 | − | − | − | − | − | − | − | − | + | + | + | | |
| EH 26 (additive effect) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | − | + |
| 6.25 | − | − | − | − | − | − | − | − | − | − | − | + | + |
| 3.13 | − | − | − | − | − | − | − | − | − | − | − | + | + |
| 0 | − | − | − | − | − | − | − | − | − | + | + | + | |

TABLE 51

| Oxethazaine | RXM (μg/ml) | | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0 |
| 89-355 (additive effect) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | − | − |
| 6.25 | − | − | − | − | − | − | − | − | − | − | + | + | + |
| 3.13 | − | − | − | − | − | − | − | − | − | − | + | + | + |
| 0 | − | − | − | − | − | − | − | − | − | + | + | + | |
| 89-357 (additive effect) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | − | + |
| 6.25 | − | − | − | − | − | − | − | − | − | − | − | + | + |
| 3.13 | − | − | − | − | − | − | − | − | − | − | − | + | + |
| 0 | − | − | − | − | − | − | − | − | − | − | + | + | |

TABLE 52

| Oxethazaine | RXM (μg/ml) | | | | | | | | | | | | |
|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0 |
| 89-360 (additive effect) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | + | + | + |
| 6.25 | − | − | − | − | − | − | − | − | − | + | + | + | + |
| 3.13 | − | − | − | − | − | − | − | − | − | + | + | + | + |
| 0 | − | − | − | − | − | − | − | + | + | + | + | | |

TABLE 52-continued

| Oxethazaine | RXM (µg/ml) | | | | | | | | | | | | |
|---|---|---|---|---|---|---|---|---|---|---|---|---|---|
| (µg/ml) | 100 | 50 | 25 | 12.5 | 6.25 | 3.13 | 1.56 | 0.8 | 0.4 | 0.2 | 0.1 | 0.05 | 0 |
| | 90-375 (additive effect) | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | − | + |
| 6.25 | − | − | − | − | − | − | − | − | − | − | − | + | + |
| 3.13 | − | − | − | − | − | − | − | − | − | − | − | + | + |
| 0 | − | − | − | − | − | − | − | − | − | − | + | + | |

TABLE 53

| Oxethazaine | RXM (µg/ml) | | | | | | | | | | | | |
|---|---|---|---|---|---|---|---|---|---|---|---|---|---|
| (µg/ml) | 100 | 50 | 25 | 12.5 | 6.25 | 3.13 | 1.56 | 0.8 | 0.4 | 0.2 | 0.1 | 0.05 | 0 |
| | 90-384 (synergism) | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | + | + |
| 6.25 | − | − | − | − | − | − | − | − | − | − | + | + | + |
| 3.13 | − | − | − | − | − | − | − | − | − | + | + | + | + |
| 0 | − | − | − | − | − | − | − | − | + | + | + | + | |
| | 90-388 (synergism) | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | + | + |
| 6.25 | − | − | − | − | − | − | − | − | − | − | − | + | + |
| 3.13 | − | − | − | − | − | − | − | − | − | + | + | + | + |
| 0 | − | − | − | − | − | − | − | − | − | + | + | + | |

TABLE 54

| Oxethazaine | RXM (µg/ml) | | | | | | | | | | | | |
|---|---|---|---|---|---|---|---|---|---|---|---|---|---|
| (µg/ml) | 100 | 50 | 25 | 12.5 | 6.25 | 3.13 | 1.56 | 0.8 | 0.4 | 0.2 | 0.1 | 0.05 | 0 |
| | 90-F390 (additive effect) | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | − | + |
| 6.25 | − | − | − | − | − | − | − | − | − | − | + | + | + |
| 3.13 | − | − | − | − | − | − | − | − | − | − | + | + | + |
| 0 | − | − | − | − | − | − | − | − | − | + | + | + | |
| | 90-392 (additive effect) | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | − | − |
| 6.25 | − | − | − | − | − | − | − | − | − | − | − | + | + |
| 3.13 | − | − | − | − | − | − | − | − | − | − | + | + | + |
| 0 | − | − | − | − | − | − | − | − | − | − | + | + | |

TABLE 55

| Oxethazaine | RXM (μg/ml) | | | | | | | | | | | | |
|---|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0 |
| 90-394 (additive effect) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | + | + |
| 6.25 | − | − | − | − | − | − | − | − | − | − | + | + | + |
| 3.13 | − | − | − | − | − | − | − | − | − | − | + | + | + |
| 0 | − | − | − | − | − | − | − | − | − | + | + | + | |
| 90-397 (synergism) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | − | + |
| 6.25 | − | − | − | − | − | − | − | − | − | − | + | + | + |
| 3.13 | − | − | − | − | − | − | − | − | − | + | + | + | + |
| 0 | − | − | − | − | − | − | − | − | + | + | + | + | |

TABLE 56

| Oxethazaine | RXM (μg/ml) | | | | | | | | | | | | |
|---|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0 |
| 90-407 (additive effect) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | + | + | + |
| 6.25 | − | − | − | − | − | − | − | − | − | + | + | + | + |
| 3.13 | − | − | − | − | − | − | − | − | − | + | + | + | + |
| 0 | − | − | − | − | − | − | − | − | + | + | + | + | |
| 90-411 (additive effect) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | − | + |
| 6.25 | − | − | − | − | − | − | − | − | − | − | − | + | + |
| 3.13 | − | − | − | − | − | − | − | − | − | − | − | + | + |
| 0 | − | − | − | − | − | − | − | − | − | − | + | + | |

TABLE 57

| Oxethazaine | RXM (μg/ml) | | | | | | | | | | | | |
|---|---|---|---|---|---|---|---|---|---|---|---|---|---|
| (μg/ml) | 100 | 50 | 25 | 12.5 | 6.25 | 3.13 | 1.56 | 0.8 | 0.4 | 0.2 | 0.1 | 0.05 | 0 |
| 90-414 (additive effect) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | − | + |
| 6.25 | − | − | − | − | − | − | − | − | − | − | − | + | + |
| 3.13 | − | − | − | − | − | − | − | − | − | − | − | + | + |
| 0 | − | − | − | − | − | − | − | − | − | − | + | + | |
| 90-428 (additive effect) | | | | | | | | | | | | | |
| 100 | − | − | − | − | − | − | − | − | − | − | − | − | − |
| 50 | − | − | − | − | − | − | − | − | − | − | − | − | − |
| 25 | − | − | − | − | − | − | − | − | − | − | − | − | − |
| 12.5 | − | − | − | − | − | − | − | − | − | − | − | + | + |
| 6.25 | − | − | − | − | − | − | − | − | − | − | + | + | + |
| 3.13 | − | − | − | − | − | − | − | − | − | − | − | + | + |
| 0 | − | − | − | − | − | − | − | − | − | + | + | + | |

As is evident from the results of antimicrobial activity test 6, further synergism and additive effect for anti-*H. pylori* activity were recognized when oxethazaine was used in combination with an antibiotic.

The results are shown in the following Table.

Effect of Combined Use of Oxethazaine and Each Antimicrobial agent

|  | Compound | | |
| --- | --- | --- | --- |
|  | AMPC | CAM | RXM |
| synergism | 0 strains/ 15 strains | 5 strains/ 21 strains | 4 strains/ 22 strains |
| additive effect | 10 strains/ 15 strains | 17 strains/ 21 strains | 19 strains/ 22 strains |

From these results, the further excellent *H. pylori*-eradicating effect of the present invention comprising combined use of oxethazaine and an antibiotic is evident, and when both the compounds are used in combination, the dose of the antibiotic administered can be reduced, and thus a reduction in side effects can be expected.

Antimicrobial Activity Test 7

Anti-*H. pylori* Activity of Oxethazaine used in Combination with a $H_2$-receptor Antagonist 1. Method The synergism of oxethazaine used in combination with cimetidine or famotidine was examined in the same manner as in antimicrobial activity test 1, using the checker board method.

2. Results

Hereinafter, the results are shown for each strain in the same manner as in antimicrobial activity test 3.

1) Cimetidine

TABLE 58

| Oxethazaine | Cimetidine (µg/ml) | | | | | |
| --- | --- | --- | --- | --- | --- | --- |
| (µg/ml) | 100 | 50 | 25 | 12.5 | 6.25 | 0 |
| NCTC11637 (additive effect) | | | | | | |
| 800 | − | − | − | − | − | + |
| 400 | − | − | − | + | + | + |
| 200 | − | − | − | + | + | + |
| 0 | − | − | − | + | + | |
| NCTC11639 (additive effect) | | | | | | |
| 800 | − | − | − | − | + | + |
| 400 | − | − | − | + | + | + |
| 200 | − | − | − | + | + | + |
| 0 | − | − | − | + | + | |
| NCTC11916 (additive effect) | | | | | | |
| 800 | − | − | − | − | + | + |
| 400 | − | − | − | + | + | + |
| 200 | − | − | − | + | + | + |
| 0 | − | − | − | + | + | |
| EH 12 (additive effect) | | | | | | |
| 800 | − | − | − | − | − | − |
| 400 | − | − | − | − | − | + |
| 200 | − | − | − | − | + | + |
| 0 | − | − | − | + | + | |

TABLE 59

| Oxethazaine | Cimetidine (µg/ml) | | | | | |
| --- | --- | --- | --- | --- | --- | --- |
| (µg/ml) | 100 | 50 | 25 | 12.5 | 6.25 | 0 |
| EH 13 (additive effect) | | | | | | |
| 800 | − | − | − | − | − | − |
| 400 | − | − | − | − | − | + |
| 200 | − | − | − | + | + | + |
| 0 | − | − | − | + | + | |
| EH 16 (additive effect) | | | | | | |
| 800 | − | − | − | − | − | + |
| 400 | − | − | − | − | + | + |
| 200 | − | − | − | − | + | + |
| 0 | − | − | − | + | + | |
| EH 26 (additive effect) | | | | | | |
| 800 | − | − | − | − | + | + |
| 400 | − | − | − | + | + | + |
| 200 | − | − | − | + | + | + |
| 0 | − | − | − | + | + | |
| 89-355 (additive effect) | | | | | | |
| 800 | − | − | − | − | − | − |
| 400 | − | − | − | − | − | + |
| 200 | − | − | − | − | + | + |
| 0 | − | − | − | − | + | |

TABLE 60

| Oxethazaine | Cimetidine (µg/ml) | | | | | |
| --- | --- | --- | --- | --- | --- | --- |
| (µg/ml) | 100 | 50 | 25 | 12.5 | 6.25 | 0 |
| 89-360 (additive effect) | | | | | | |
| 800 | − | − | − | − | + | + |
| 400 | − | − | − | + | + | + |
| 200 | − | − | − | + | + | + |
| 0 | − | − | + | + | + | |
| 90-384 (additive effect) | | | | | | |
| 800 | − | − | − | − | + | + |
| 400 | − | − | − | + | + | + |
| 200 | − | − | − | + | + | + |
| 0 | − | − | − | + | + | |
| 90-390 (additive effect) | | | | | | |
| 800 | − | − | − | − | + | + |
| 400 | − | − | − | + | + | + |
| 200 | − | − | − | + | + | + |
| 0 | − | − | − | + | + | |
| 90-392 (additive effect) | | | | | | |
| 800 | − | − | − | − | − | + |
| 400 | − | − | − | − | + | + |
| 200 | − | − | − | − | + | + |
| 0 | − | − | − | + | + | |

TABLE 61

| Oxethazaine | Cimetidine (µg/ml) | | | | | |
| --- | --- | --- | --- | --- | --- | --- |
| (µg/ml) | 100 | 50 | 25 | 12.5 | 6.25 | 0 |
| 90-394 (additive effect) | | | | | | |
| 800 | − | − | − | − | + | + |
| 400 | − | − | − | + | + | + |
| 200 | − | − | − | + | + | + |
| 0 | − | − | − | + | + | |

TABLE 61-continued

| Oxethazaine | Cimetidine (μg/ml) | | | | | |
|---|---|---|---|---|---|---|
| (μg/ml) | 100 | 50 | 25 | 12.5 | 6.25 | 0 |
| 90-397 (additive effect) | | | | | | |
| 800 | − | − | − | − | + | + |
| 400 | − | − | − | + | + | + |
| 200 | − | − | − | + | + | + |
| 0 | − | − | − | + | + | |
| 90-407 (additive effect) | | | | | | |
| 800 | − | − | − | − | + | + |
| 400 | − | − | − | + | + | + |
| 200 | − | − | − | + | + | + |
| 0 | − | − | − | + | + | |
| 90-411 (additive effect) | | | | | | |
| 800 | − | − | − | − | + | + |
| 400 | − | − | − | + | + | + |
| 200 | − | − | − | + | + | + |
| 0 | − | − | − | + | + | |

TABLE 62

| Oxethazaine | Cimetidine (μg/ml) | | | | | |
|---|---|---|---|---|---|---|
| (μg/ml) | 100 | 50 | 25 | 12.5 | 6.25 | 0 |
| 90-414 (additive effect) | | | | | | |
| 800 | − | − | − | − | − | − |
| 400 | − | − | − | − | − | + |
| 200 | − | − | − | − | + | + |
| 0 | − | − | − | + | + | |
| 90-428 (additive effect) | | | | | | |
| 800 | − | − | − | − | + | + |
| 400 | − | − | − | + | + | + |
| 200 | − | − | − | + | + | + |
| 0 | − | − | − | + | + | |

2) Famotidine

TABLE 63

| Oxethazaine | Famotidine (μg/ml) | | | | | |
|---|---|---|---|---|---|---|
| (μg/ml) | 100 | 50 | 25 | 12.5 | 6.25 | 0 |
| NCTC11637 (additive effect) | | | | | | |
| 800 | − | − | − | − | + | + |
| 400 | − | − | − | + | + | + |
| 200 | − | − | − | + | + | + |
| 0 | − | − | − | + | + | |
| NCTC11639 (additive effect) | | | | | | |
| 800 | − | − | − | − | − | + |
| 400 | − | − | − | + | + | + |
| 200 | − | − | − | + | + | + |
| 0 | − | − | − | + | + | |
| NCTC11916 (additive effect) | | | | | | |
| 800 | − | − | − | + | + | + |
| 400 | − | − | − | + | + | + |
| 200 | − | − | − | + | + | + |
| 0 | − | − | − | + | + | |
| EH 12 (additive effect) | | | | | | |
| 800 | − | − | − | − | + | + |
| 400 | − | − | − | + | + | + |
| 200 | − | − | − | + | + | + |
| 0 | − | − | − | + | + | |

TABLE 64

| Oxethazaine | Famotidine (μg/ml) | | | | | |
|---|---|---|---|---|---|---|
| (μg/ml) | 100 | 50 | 25 | 12.5 | 6.25 | 0 |
| EH 13 (additive effect) | | | | | | |
| 800 | − | − | − | − | + | + |
| 400 | − | − | − | + | + | + |
| 200 | − | − | − | + | + | + |
| 0 | − | − | − | + | + | |
| EH 16 (additive effect) | | | | | | |
| 800 | − | − | − | − | + | + |
| 400 | − | − | − | + | + | + |
| 200 | − | − | − | + | + | + |
| 0 | − | − | − | + | + | |
| EH 26 (additive effect) | | | | | | |
| 800 | − | − | − | − | + | + |
| 400 | − | − | − | + | + | + |
| 200 | − | − | − | + | + | + |
| 0 | − | − | − | + | + | |
| 89-357 (additive effect) | | | | | | |
| 800 | − | − | − | − | + | + |
| 400 | − | − | − | + | + | + |
| 200 | − | − | − | + | + | + |
| 0 | − | − | − | + | + | |

TABLE 65

| Oxethazaine | Famotidine (μg/ml) | | | | | |
|---|---|---|---|---|---|---|
| (μg/ml) | 100 | 50 | 25 | 12.5 | 6.25 | 0 |
| 89-360 (additive effect) | | | | | | |
| 800 | − | − | − | − | + | + |
| 400 | − | − | − | + | + | + |
| 200 | − | − | − | + | + | + |
| 0 | − | + | + | + | | |
| 90-390 (additive effect) | | | | | | |
| 800 | − | − | − | − | + | + |
| 400 | − | − | − | + | + | + |
| 200 | − | − | − | + | + | + |
| 0 | − | − | − | + | + | |
| 90-392 (additive effect) | | | | | | |
| 800 | − | − | − | − | + | + |
| 400 | − | − | − | + | + | + |
| 200 | − | − | − | + | + | + |
| 0 | − | − | − | + | + | |
| 90-397 (additive effect) | | | | | | |
| 800 | − | − | − | − | + | + |
| 400 | − | − | − | + | + | + |
| 200 | − | − | − | + | + | + |
| 0 | − | − | − | + | + | |

TABLE 66

| Oxethazaine | Famotidine (μg/ml) | | | | | |
|---|---|---|---|---|---|---|
| (μg/ml) | 100 | 50 | 25 | 12.5 | 6.25 | 0 |
| 90-407 (additive effect) | | | | | | |
| 800 | − | − | − | − | + | + |
| 400 | − | − | − | + | + | + |
| 200 | − | − | − | + | + | + |
| 0 | − | − | − | + | + | |

TABLE 66-continued

| Oxethazaine | Famotidine (μg/ml) | | | | | |
|---|---|---|---|---|---|---|
| (μg/ml) | 100 | 50 | 25 | 12.5 | 6.25 | 0 |
| 90-411 (additive effect) | | | | | | |
| 800 | − | − | − | − | + | + |
| 400 | − | − | − | + | + | + |
| 200 | − | − | − | + | + | + |
| 0 | − | − | − | + | + | |
| 90-414 (additive effect) | | | | | | |
| 800 | − | − | − | − | + | + |
| 400 | − | − | − | + | + | + |
| 200 | − | − | − | + | + | + |
| 0 | − | − | − | + | + | |

As is evident from the result of antimicrobial activity test 7 mentioned above, further synergism and additive effect for anti-*H. pylori* activity were recognized when oxethazaine was used in combination with the $H_2$-receptor antagonist.

The results are shown in the following Table.

Effect of Combined Use of Oxethazaine and $H_2$-receptor Antagonist

| | Compound | |
|---|---|---|
| | Cimetidine | Famotidine |
| additive effect | 18 strains/18 strains | 15 strains/15 strains |

From these results, the further excellent *H. pylori*-eradicating effect of the present invention comprising combined use of oxethazaine and the $H_2$-receptor antagonist is evident, and when both the compounds are used in combination, the dose of the $H_2$-receptor antagonist administered can be reduced, and thus a reduction in side effects can be expected.

Next, the antimicrobial activity (MIC, μg/ml) of oxethazaine and structures analogues against Gram-positive bacteria, which was evaluated in a usual manner, is shown below.

| | | Compound | | | |
|---|---|---|---|---|---|
| Strain No. | Oxethazaine | (A) | (B) | (C) | (D) |
| *S. aureus* FDA 209-P | 12.5 | >100 | >100 | >100 | >100 |
| *S. epidermidis* ATCC 12228 | 6.25 | >100 | >100 | >100 | >100 |
| *E. faecalis* RIMD 3116001 | 25 | >100 | >100 | >100 | >100 |

Compound (A): ethyl p-aminobenzoate
Compound (B): ethyl piperidinoacetylaminobenzoate
Compound (C): procaine hydrochloride
Compound (D): lidocaine injection From the results described above, it is evident that oxethazaine exhibits excellent effect not only on *H. pylori* but also on Gram-positive bacteria.

Finally, the results of an acute toxicity test of oxethazaine are shown below.

Acute Toxicity Test

A toxicity test was conducted by orally administering a single dose into 7- to 8-weeks old Slc:SD rats and Slc:ICR mice, each group consisting of 5 females and 5 males (medium; physiological saline).

$LD_{50}$ values are shown in the following table.

| Animal | Mouse | | Rat | |
|---|---|---|---|---|
| Sex | ♂ | ♀ | ♂ | ♀ |
| $LD_{50}$ (mg/kg) (Oral administration) | 1231 | 1000 ~2000 | 1000 ~2000 | 1071 |

These $LD_{50}$ values are about 5000 times as high as clinical doses (15 to 40 mg/day) in oral administration, indicating extremely high safety.

Further, as is evident from Examples mentioned above, the compound of the present invention has *H. pylori*-eradicating action equal to or higher than that of antibiotics, and is thus useful as an antimicrobial agent for preventing, ameliorating and treating peptic ulcer and gastritis attributable to *H. pylori*, particularly recurring ulcer and recurring gastritis.

Specifically, it can be administered for a long time as a highly safe antimicrobial agent which can prevent, improve and treat peptic ulcer and gastritis by inhibiting gastric acid secretion, and also recurring ulcer and gastritis caused by *H. pylori*, without simultaneously using antibiotics.

The dose of the compound of the present invention administered as an antimicrobial agent to a patient varies depending on symptoms, the type and progress of gastric ulcer and gastritis, the age, and cardiac, hepatic and renal functions of the patient, and is not particularly limited. However, it is preferable that oxethazaine is administered to an adult usually in a dose of 1 to 100 mg/day, more preferably 15 to 40 mg/day. Further, when oxethazaine and PPI are used in combination, oxethazaine is combined with PPI in a dose of 0.01 to 100 mg/day, preferably 0.1 to 80 mg, more preferably 1.0 to 60 mg, further preferably 5 to 40 mg, and both the compounds are orally administered.

As the administration form, for example, powder, fine particles, granules, tablets and capsules etc. maybe proposed. In pharmaceutical manufacturing, the pharmaceutical preparation can also be produced in a usual manner by using usual pharmaceutical carriers, but according to a method described in JP-A 1-290628 or JP-A 2-22225, PPI can be formed into a more stable pharmaceutical preparation.

As described above, the excellent anti-*H. pylori* effect and safety of the present invention were proved.

What is claimed is:

1. A method of treating a microbiological infection caused by *Helicobacter pylori*, which comprises administering to a patient suffering therefrom an effective amount of a proton pump inhibitor selected from the group consisting of 2-[4-(3-methoxypropoxy)-3-methylpyridine-2-yl]methylthio-1H-benzimidazole (I), omeprazole (II) and lansoprazole (III) represented by the following chemical formulae:

I

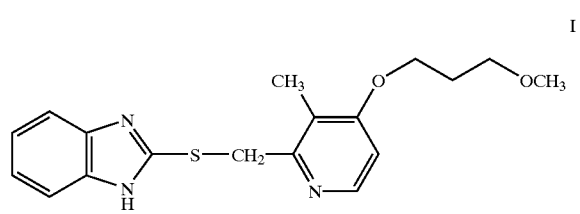

-continued

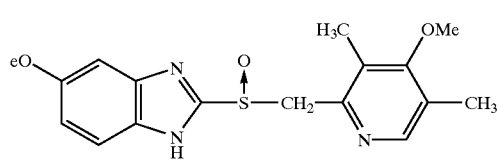

Omeprazole (III)

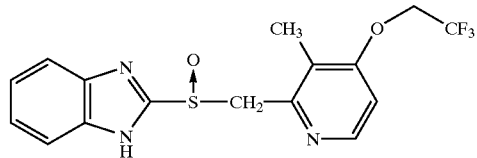

Lansoprazole and pharmacologically acceptable salts thereof and an effective amount of an oxethazaine antimicrobial agent represented by the following formula:

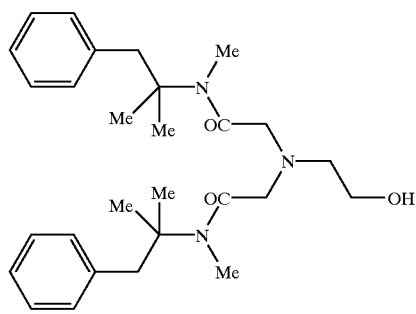

as an active ingredient.

2. The method as claimed in claim 1, which comprises administering oxethazaine and 2-[4-(3-methoxypropoxy)-3-methylpyridine-2-yl]methylthio-1H-benzimidazole (I) or its pharmacologically acceptable salt as active ingredients.

3. The method as claimed in claim 1, which comprises administering oxethazaine and omeprazole (II) or its pharmacologically acceptable salt.

4. The method as claimed in claim 1, which comprises administering oxethazaine and lansoprazole (III) or its pharmacologically acceptable salt.

* * * * *